(12) United States Patent
Boehm

(10) Patent No.: US 8,500,812 B2
(45) Date of Patent: Aug. 6, 2013

(54) DEVICE AND METHOD FOR IMPLANTATION THAT RESTORES PHYSIOLOGIC RANGE OF MOTION BY ESTABLISHING AN ADJUSTABLE CONSTRAINED MOTION OF THE SPINE WITHOUT INTRUSION OF ASSOCIATED FACET JOINTS

(75) Inventor: Frank H. Boehm, Utica, NY (US)

(73) Assignee: Corporate Venture Services Inc., Utica, NY (US)

( * ) Notice: Subject to any disclaimer, the term of this patent is extended or adjusted under 35 U.S.C. 154(b) by 846 days.

(21) Appl. No.: 12/414,460

(22) Filed: Mar. 30, 2009

(65) Prior Publication Data

US 2009/0270917 A1 Oct. 29, 2009

Related U.S. Application Data

(63) Continuation-in-part of application No. 11/224,009, filed on Sep. 13, 2005, now abandoned.

(60) Provisional application No. 61/064,849, filed on Mar. 31, 2008.

(51) Int. Cl.
*A61B 17/70* (2006.01)

(52) U.S. Cl.
USPC .................. 623/17.11; 606/246; 606/247

(58) Field of Classification Search
USPC ........................................... 606/248
See application file for complete search history.

(56) References Cited

U.S. PATENT DOCUMENTS

| 5,674,296 | A | 10/1997 | Bryan et al. |
| 2003/0055427 | A1* | 3/2003 | Graf ............................ 606/61 |
| 2007/0073290 | A1 | 3/2007 | Boehm, Jr. |
| 2007/0225712 | A1 | 9/2007 | Altarac et al. |

OTHER PUBLICATIONS

International Searching Authority, International Search Report and Written Opinion in PCT No. PCT/US2009/038829, Mailed Nov. 16, 2009.

* cited by examiner

*Primary Examiner* — Bruce E Snow
*Assistant Examiner* — Brian Dukert
(74) *Attorney, Agent, or Firm* — Hiscock & Barclay, LLP

(57) ABSTRACT

Disclosed in this specification are device and method that provides for adjustable, constrained motion of a spinal motion segment that is affected by degenerative disease, microinstability and the like. The device has first and second diagonal connectors, the leading ends of which are disposed within first and second fluid chambers of a housing unit. A liner is provided in the fluid chambers which are accessible through access ports into the housing unit.

1 Claim, 22 Drawing Sheets

DEVICE AND METHOD FOR IMPLANTATION THAT RESTORES PHYSIOLOGIC RANGE OF MOTION BY ESTABLISHING AN ADJUSTABLE CONSTRAINED MOTION OF THE SPINE WITHOUT INTRUSION OF ASSOCIATED FACET JOINTS

CROSS-REFERENCE TO RELATED APPLICATIONS

This application is a continuation-in-part of U.S. patent application Ser. No. 11/224,009 (filed Sep. 13, 2005, now abandoned) and claims priority to and the benefit of U.S. provisional application Ser. No. 61/064,849 (filed Mar. 31, 2008) the contents of which are incorporated herein by reference.

BACKGROUND

Backache is one of the oldest and most ubiquitous complaints offered by patients to their physicians. After the common cold, it is the most common reason for Americans to seek medical attention, and it is the most common cause of disability not only in America but in most technologically developed countries. The costs associated with the overall medical and surgical treatment of back pain in the United States are currently estimated at a staggering $90 B annually, and this does not begin to measure the loss of wages and productivity, as well as disability benefits, legal costs, and other expenses borne by the system. Overall, the global cost of back pain in America is virtually immeasurable.

The earliest records of interactions between physicians and their patients, including records from the Egyptian artifacts such as the famous Edwin Smith Papyrus, discuss maladies affecting the spine. There are references to backaches seen in some of the earliest writings from the land of Sumer, as well as a wealth of literature discussing a variety of potions and methods of relief of back pain that can be found in the literature of the ancient Indian medicine, which dates as far back as four thousand years. Despite the broad centuries and advances in medical science, there is no clear, universally accepted explanation for back pain secondary to degenerative disease. This definition fully recognizes and excludes the many instances in which back pain has a very clearly defined pathologic basis (i.e. tumor, fracture, nephrolithiasis, infection, disorders of the internal organs such as penetrating duodenal ulcers and so forth).

The first scientific attempts at understanding back pain resulting from degenerative changes or "arthritis," came soon after the introduction of the x-ray by Roentgen in 1897. With this new tool, the types of changes that were associated with degenerative changes were observed and quickly characterized in the endplates, disc spaces, and facet joints. Soon it was appreciated that if a patient with chronic back pain and severe degenerative changes was followed with serial x-rays, a subset of these patients would ultimately report improvement if autofusion was observed in one or more segments.

These observations led to the speculation that lower back pain associated with degenerative disease is the result of excessive or abnormal movement of the vertebrae as they related to one another, resulting from relative incompetence of the disc and facet joints as the degenerative process advances. Extrapolating from this, surgical fusion of the spine was first introduced as a treatment option for patients with degenerative disease of the spine in the early part of the 20$^{th}$ century. The early reports of some success with spine fusion further helped support these contentions.

However, this is obviously vastly over-simplifying both the biomechanic and global physiologic scheme of the spine. The spine is a superbly (probably divinely) engineered articulated column, which is designed, in its ideal embodiment, to subserve a number of functions. Most importantly, it serves as a protective encasement for the most delicate structure in nature, the human spinal cord, and the associated nerves comprising the Cauda Equina, providing protection for these structures while at the same time providing some flexibility and maneuverability to the individual. This flexible column is actually a stronger structure than a solid tubular structure, allowing this column to accommodate a variety of movements that the individual might undertake during the course of their lifetime. Obviously, such flexibility is also providing the individual with an adaptive advantage, recognizing the evolutionary contribution of the vertebrate spinal column. Furthermore, the spinal column provides a centering anchor for the physiologic chassis of the individual, thus supplying the individual with axial support.

Further adding to the biomechanical complexity of this structure, we noted that the human vertebral column is composed of 24 mobile and 9 fused vertebrae, with over 70 mobile joints and hundreds of attendant muscles and ligaments. It has become clear, as the knowledge of this biomechanical structure has expanded, that all of these components contribute to the proper biomechanical function of the spine. And, as a corollary, it is now being appreciated that abnormal function of any of these structures, alone or in combination, can result in back pain. Finally, there is a rich network of fine perforating nerves that encase the discs, epidural space, and facet joints. While many of these nerves are involved in the biofeedback processes that govern the spine and help maintain its ideal biomechanical adaptability, there is also a rich network of pain sensing fibers. These fibers, designed to inform the individual of derangements of the structures that contribute to the biomechanical patency of the spine, are obviously the final common pathways for the transmission of pain fibers. Understanding the fundamentals of how these nerves work, and why they ultimately transmit the sensation of back pain, is in its very infancy at this point.

While there is still a great deal to be learned in terms of the spinal biomechanics, there are certain fundamentals that are recognized by consensus as an acceptable foundation for this knowledge. At the heart of any discussion regarding spinal biomechanics are the essential concepts of "spinal stability" as well as "spinal instability." While many volumes have been written about what ultimately comprises spinal stability, this still remains widely debated, even amongst experts.

However, most agree that the term "spinal instability," reflects a condition in which the normal, physiologic movement of one or more segments of the spine has been replaced by a movement which is either excessive, or of an abnormal rotational or translational nature. The signature that excessive, translational, or rotational movement has become pathologic is either the production of (a) one or more neurological deficits associated with this abnormal movement; or (b) the appearance of reliably reproducible pain associated with that excessive movement.

In order to better comprehend these complex concepts, one useful paradigm that has been proposed is known as the "motion segment." The motion segment by definition refers to any pair of adjacent mobile vertebrae of the spine, along with their intervening disc joint, associated facet joints, ligaments, tendons, muscles, and their exiting nerve roots and neural elements. Using this paradigm, one can attempt to first understand spinal biomechanics at a single level prior to attempting to understand the biomechanics of this articulated column as a whole. In order to do so, one must first appreciate that there is a range of normal movements that are necessary for the execution of the activities of daily existence.

In this range of normal movements, each motion segment is thought to contribute to the movements of the spinal column as a whole; in the first of these movements that we shall consider, when the individual leans forward, as though attempting to touch one's hands to one's toes, the spinal column assumes flexion. In flexion, presumably there is a foreshortening of the anterior aspect of the intervertebral disc space with somewhat of a distraction of the posterior elements of the motion segment—i.e. the spinous processes and the facet joints.

The converse of flexion is extension, in which the individual arches backwards as though to look skyward. Examining extension at the motion segment level, we see that the opposite of flexion now occurs—the spinous processes will somewhat approximate each other, and the anterior aspect of the disc will widen slightly. In addition, there is also lateral rotation and lateral bending. In lateral rotation, the torso is rotated around a theoretical axis directed along a craniocaudal axis through the mid-portion of the body. In lateral rotation, the shoulders and hips are rotated in such a fashion that the shoulder and hip on the side being rotated toward are drawn somewhat posteriorly, while the opposite shoulder and hip are drawn somewhat anteriorly; in true rotation, the ipsilateral shoulder is somewhat more posterior than the ipsilateral hip, while the contralateral shoulder is somewhat more anterior than the contralateral hip. In lateral bending, one will bring one arm towards the ipsilateral foot while elevating the opposite shoulder. By examining the body mechanics themselves, one can extrapolate the way that an individual motion segment would accommodate these movements.

Many detailed studies have been performed to identify the typical range of movement for these various normal physiologic movements. The problem, adding to the complexity of the biomechanical discussion, is that since human beings (and presumably their spines) come in many different sizes and shapes, attempting to postulate a "normal" range of movement can result in a number of inaccuracies. Rather, one must accept that to some degree, normal may often apply to normal for that individual, although there are certain basic standards that are going to be present throughout a broad range of the population.

With this as a foundation, we can now consider abnormal movements. For the purposes of this discussion, the abnormal movements under discussion would fall principally into two general categories:

1. An excessive amount of one of the natural movements that a motion segment is imbued with—i.e. flexion, extension, lateral rotation or lateral bending; and
2. An unnatural or non-physiologic movement between two vertebrae as they relate to one another, such as translation.

It has already been previously stated that the amount of flexion, extension, lateral rotation, or lateral bending that is considered "excessive" varies substantially according to a patient's age, gender, and body habitus. It is ultimately, to some degree, a surgeon's judgment that determines "excessive" movement in one of these spheres of motion.

On the other hand, with respect to the second category, these movements are truly non-physiologic insofar that there are no mechanisms in the anatomy or physiology of the spine providing for such movements, nor are there any circumstances by which the spine would ever assume these movements.

The principle abnormal movement that is often under consideration is referred to, as translational movement. In general, the term "translational movement" refers to a pathologic condition in which one vertebra will transpose itself along either an anteroposterior axis or a lateral axis, while maintaining the same general orientation with respect to the craniocaudal axis. A typical example of translation is the condition known as spondylolisthesis. In a typical spondylolisthesis, the anterior aspect of one vertebra demonstrates an anticipated profile, as viewed in the lateral plane, but the entire vertebral body is shifted anteriorly, with respect to the next vertebra above or below. In other words, translation refers to an anteroposterior or lateral shift of one vertebra with respect to the other, while maintaining its primary craniocaudal orientation within the spinal axis. It is believed that subtle translational instability (perhaps even so subtle that good diagnostic evaluations to determine the presence of such a translational instability are not yet available to clinicians) may be responsible for a great deal of back pain associated with degenerative disease.

Yet another type of abnormal movement is rotational movement. In rotational movement, the motion segment demonstrates a situation in which one of the vertebrae will rotate around a hypothetical axis that is oriented in a craniocaudal direction and passes through the mid portion of the vertebral bodies of both vertebrae. The rotating vertebrae assumes movement which is similar to that which might be seen in lateral rotation, except in pathologic rotational movement, there is far excessive displacement of the vertebra with perhaps a relative disarticulation of one facet joint and relative obscuration of the other facet joints.

In addition to these movements, there are abnormal postures of the spine such as scoliosis, kyphosis, and excessive lordosis. These terms will be generally discussed below, but are not necessarily germane to a discussion functioning around the biomechanics of a motion segment.

Therefore, when examining this range of theoretic movements that a particular motion segment can undergo, one can then anticipate that nature would provide modulators of these movements, specifically designed to govern these movements and maintain them within the normal sphere of acceptable ranges of movement. The two chief governors of movements are the intervertebral disc joint, and the bilateral posterolateral facet joints. What is of particular importance is that these articulations do not exist in vacuum, exerting their effects on the movements of the spine in an isolated fashion as was once speculated; rather, these structures clearly work in a reciprocal fashion. While a large amount of attention has traditionally been given to the intervertebral disc joint, in recent years, the critical role of the facet joints has become increasingly recognized and appreciated.

In understanding the variable contribution that each of these lends to the physiologic range of motion, it appears in further analysis that in terms of flexion, or forward bending of the spine, the disc is probably the single most important modulator. Conversely, in extension, or backward bending of the spine, the facet joints appear to be particularly important. The role of the facet joints has been proven to be especially significant in biomechanical models and spinal lab models, where it has been extensively studied and shown that at a certain point of extension, the facet joints will essentially mechanically prevent any further extension. Lateral rotation and lateral bending appear to be a combination of input from the facet joints and the disc joint. In general, the current wisdom in spinal surgery contends that the progression of degenerative disease of the spine is characterized by laxity of associated ligaments, as well as loss of competency of the disc joints and facet joints resulting in excessive movement of the spine.

Yet another important consideration in studying the motion segment model is the neuroforamina, the canals through which the nerve roots exit the spinal canal. Theoretically, any condition incarcerating the exiting nerve roots can putatively lead to radicular symptoms. In recent years, it has become recognized that a number of pathologic processes can affect these foramina, including primary foraminal stenosis, as well as narrowing of the neuroforamina secondary to degenerative collapse of the disc. Every spine surgeon has encountered patients with virtually completely collapsed discs, particularly at L4-5 and L5-S1. What is now being recognized is that when this occurs, there is clearly a reduction in the size of the neuroforamina, which may be responsible for radicular symptoms in cases such as this. One surgical principle that remains somewhat controversial is the value of distraction of a collapsed disc with a relative restoration of the disc height. While this does remain controversial, from an anecdotal perspective, every spine surgeon has seen patients in whom elevation of the disc height and enlargement of the foramina does result in remarkable improvement of the symptoms.

Therefore, armed with at least this rudimentary understanding of spinal biomechanics, one can began to introduce rationale into the operative approaches that might be undertaken in patients with degenerative spinal disease.

Certainly, it at least appears logical and intuitive that when any anatomy is disordered, one basic principle of surgery would be to restore the anatomy to as "normal" as can possibly be achieved. This, of course, must be evaluated bearing in mind that in most instances, another principle of surgery is to remove as much pathologic tissue as possible. It is important to note that perhaps more in spinal surgery than in any other surgical subspecialty, the surgical treatment of advanced degenerative disease results in the removal of very extensive pathologically altered but "normal" anatomic tissues. With this type of procedure, there has been such extensive derangement that the normal anatomy can no longer be restored. Hence, one returns to the role that surgical fusion may play in attempting to provide the patient with at least some symptomatic results.

In a case such as that described, namely, extensive surgical removal of advanced pathologic disease, it is felt by many experts in the field that simply removing the pathologic tissue is an acceptable surgical procedure. This is typified by the multi-level laminectomy without fusion, the surgical approach that has been traditionally taken by many surgeons in the treatment of multi-level spinal steno sis, which is a time-honored operative approach to this problem that was considered satisfactory in many patients with advanced stenosis. However, that was partly because this population is often elderly and is not very physically active, either before or after the surgery.

But the demographics of spinal disease are clearly shifting. One important factor to consider is the changing profile of the aging population, here in the United States and around the world. In the United States, not only is the population aging, such that the median life expectancy has risen significantly over the past few decades, but also, we are seeing a population that is much more active more into their $7^{th}$ and even $8^{th}$ decades of life. This has had a clear effect on the philosophy governing surgeries for spinal stenosis. As mentioned previously, when the surgical approach to spinal stenosis was first being evaluated and undertaken, a multi-level laminectomy was the gold standard for surgical treatment, and it was clearly enough, as these patients were satisfied to live out their life in a relatively sedentary fashion.

However, in today's world, as mentioned above, there is a significant increase in the physical activities of the elderly population. This has resulted in a fundamental shift in the philosophy of this type of surgery. Clearly, doing a multi-level laminectomy in someone who is planning to continue to be very active is fraught with potential long term complications. Not only do these patients complain of a greater incidence of back pain after this type of surgery; more critically, a percentage of these patients develop translational and rotational abnormalities such as postoperative spondylolisthesis, kyphosis, or rotoscoliosis. With these potential complications, many surgeons now clearly favor an approach that incorporates fusion into the surgical philosophy.

However, the elderly population with spinal stenosis is clearly not the only cohort for which fusion is considered, and, in fact, represents the minority of patients. Again, with the shifting demographics including overall increase in the recreational physical activities of patients, high velocity motor vehicle accidents, and the ever increasing stresses of manual labor jobs, more and more young and middle aged patients are developing advanced disc disease, with a significant component of back pain. Returning to the original thesis put forth in this section, the current philosophy suggests that a major cause of back pain in that setting is microinstability and subtle translational movements that are seen in association with this advanced disc degeneration. Osteophytic spurring often seen on the anterior and posterior surfaces of these vertebral bodies is highly suggestive of this type of microinstability. In a patient with a clinical presentation that include back pain, with or without leg pain, in association with degenerative disc disease, loss of disc height, and at least inferential evidence of microinstability, it is now considered a very reasonable approach to move ahead with a spinal fusion, thus eliminating all movement from the motion segment in question. The pervasiveness of this surgical philosophy has lead to an almost logarithmic increase in spinal fusions over the past two decades, although more recently, these numbers have begun to stabilize. Currently, in the United States, an average of 300-400,000 spinal fusions is performed every year.

Again, it can be recalled that the theory of a spinal fusion is to eliminate excessive motion at a motion segment, simply by eliminating all motion. However, this then raises the question of the effect of this type of change on spinal dynamic might have on the intervertebral discs and facet joints at the next level above and/or below the fused disc. Bioengineering and biomechanics would dictate that fusing one level would have a relatively strong increase on the stress at the levels that are immediately adjacent to it and there have been some studies that have shown that there is an accelerated degeneration in discs that are adjacent to spinal fusions.

Obviously, there are also shortcomings with fusion, and many patients that have had a spinal fusion performed report chronic ongoing back pain well after otherwise recovering in an uneventful fashion. Of course, from both a bioengineering and intuitive perspective, obviously the most ideal approach that could be undertaken would be re-establishing the normal motion at the diseased or target motion segment. This would obviously satisfy even more of the biodynamic factors than a fusion, and would avoid the speculation that fusion leads to "adjacent disc disease." Far more important, however, is the theoretical advantage of restoring/maintaining "normal" spinal dynamics, whatever this euphemism will ultimately be determined to imply.

It is interesting to note the correlation between the evolutions of the philosophies guiding the surgical treatment of arthritis affecting major joints and the philosophies guiding the treatment of spinal degenerative disease. The earliest surgical treatments of severe degenerative disease of the hip or knee joints typically involved fusion of these major joints. In that fashion, the pain from movement of the diseased joints was relieved by removing all motion from the joint. However, by the mid-1960's total hip joint replacement had been introduced, and total knee joints were introduced soon after. By the introduction of such devices it was thought that rather than losing the movement of these joints, returning the motion of the joint to a relatively normal range resulted in much better long-term results.

Pursuant to that philosophy, surgeons have been proposing various types of disc prosthesis for a number of years now. As far back as 1964, several Scandinavian surgeons attempted to address this problem by placing a steel ball or sphere in the center of a disc after removal had been completed. At least in the earliest part of this series (apparently, a total of 19 patients were treated in this fashion), no fixation device whatsoever was used, and the discs were merely distracted and the ball was placed into position. This experimental protocol as ultimately discontinued, but these surgeons recognized and demonstrated the need for an artificial disc of some kind. Of interest, there are at least two of these patients that remain with this sphere in place who are reported to still be doing very well.

In the 1980's, at the Charite' Hospital in Germany, a somewhat more sophisticated artificial disc was ultimately developed, and has been placed in several thousand patients in the 17 years since it was first introduced. This has recently been introduced in the United States as well, and has been cleared for clinical use on a non-trial basis. In this way, the theory is that even a badly diseased disc can be removed and hopefully, the natural movement of the lumbar spine can be recapitulated.

However, this Charite' disc is unfortunately, not without its issues and complications as well. Although the interpretation of the statistics is certainly subject to individual understanding, there is without question a number of patients who continue to do poorly, even after the placement of the Charite' disc. Nevertheless, this was essentially the first device introduced for clinical use, which attempted to speak to the issue of preserving spinal motion and returning it to normal. Since the introduction of the Charite' discs, a number of other devices designed to achieve "total disc replacement" have been brought to clinical trials, with many other devices essentially being proposed.

It is very clear, however, that spinal dynamics are of a sufficient level of complexity that these types of first and second generation devices are not going to be able to fully accommodate the demands placed on such theoretical device. Without question, further development is needed and the technology is probably years, if not a decade, away from a fully functional artificial disc that would truly satisfy all of the obligations and requirements placed upon it.

Spinal dynamics are clearly much more complicated than the dynamics at other joints, including the hip. There are multiple, complex reasons for this, but some of these reasons include the fact that any one (disc or facet) joint in the spine is, first of all, dependent on the actions of similar joints in the immediate areas (superior and inferior to the joint(s) in question), and probably, at least to a limited degree, to most of the other joints in the spine. Additionally, it is well-recognized that the dynamics that come to bear upon the spine are amongst the most complex biomechanical systems in the body.

One of the reasons why an artificial disc presents such a challenge to bioengineering is because of the many different and varying dynamic requirements and demands that are placed on the human discs. The load that it bears varies significantly depending on if the subject is lying, sitting or standing, as well as whether or not the subject is bearing any weight such as holding any additional weight. As a subject changes position (i.e. going from a crouched to a standing position) the internal pressure of the disc, as well as the dynamics of the motion segment will alter significantly. This is even further augmented by performing such a maneuver while bearing weight. The mechanical devices of the first and second generation artificial discs, which are currently on the market, do not have the wide range of responses to these many different mechanical stresses. Rather, these devices will respond to a very specific sequence of stressors, thus making them subject to mechanical fatigue over time. In addition, other problems may eventually present themselves including subsidence around the disc or alternatively possibly even autofusion. It should be noted that there have been several cases of autofusion of the cervical discs reported in the literature, and the mechanics and the biologic milieu for the theoretic basis of autofusion are very clear.

Additionally, there are probably no joints in the body that must move in as many planes and respond to shear stressors or load bearing in as many different planes as the intervertebral disc, with the lumbar intervertebral discs obviously subjective to the greatest pressures. In a word, the biomechanical demands on the intervertebral discs cannot be overstated. Yet another challenge to the artificial disc technology rests in the fact that the current state of knowledge regarding the pathophysiology and morphogenesis of degenerative disc disease remains in its infancy. As has been previously mentioned, there is data and evidence that is now coming to attention that suggests that degenerative disc disease is at least, in part, possibly related to a vasculopathy of the endplates. In that instance, it is not likely that an artificial disc is going to make much difference and degenerative processes will continue, in with the artificial disc in place. Over the long term, this could have significant, adverse effects on a level in which an artificial disc has been placed.

On the other hand, the theoretic basis of the use of an artificial disc, specifically the preservation of the natural motion of a motion segment, can be appreciated with great clarity. On the grandest hypothetical level, it certainly would be best to preserve motion in a structure that is as dynamic as the spinal column. We can only begin to speculate at the advantages of doing so, including the theoretic possibility of mechanically stressing levels above and below a fusion (as opposed to preserving the motion) as well as the possible salutatory effects on the spinal column as whole, and the issues regarding endplate vascular compromise.

It can be appreciated that the state of the art confirms what has already been hypothesized above: that as degenerative disease of the spine advances, normal movement at any level affected by this advancing disease is replaced by increased movement—indeed, ultimately pathologic movement.

One other issue that must be addressed is the fact that the actual surgical procedure for placement of an artificial disc, particularly in the lumbar spine, is a somewhat heroic effort. It requires an anterior transabdominal or retroperitoneal approach to the disc space in question, and particularly in the setting of an L4-5 operation, carries with it the potential risk of catastrophic or even lethal vascular injury to structures such as the aorta, the inferior vena cava, or the iliac vessels. Hence, the surgical, technical, and anesthetic challenges will sometimes disqualify a patient from the surgery who would otherwise greatly benefit from a motion preserving technology.

This creates a dilemma for many surgeons, such that many surgeons agree with the theoretic basis and indications for disc replacement, but are concerned with undertaking such a significant surgical procedure in order to place a device that may not truly accomplish the desired endpoints. Furthermore, in a number of cases, patients are not medically capable of tolerating this surgical procedure and its attendant anesthesia.

In an effort to identify technologies that offer motion preservation but are not attended by the technical challenges, it has been postulated that posterior motion preservation technologies may be an attractive alternative in certain instances. These systems are being euphemistically referred to as "dynamic stabilization" systems, although, in the end, analysis of such nomenclature demonstrates it to be oxymoron (dynamic=movement; stabilization=prevention of movement). However, semantics aside, what these systems are intended to do is to provide a system that utilizes the pedicles to anchor the device which then reduces excessive movements of a particular motion segment. Such a system might also provide an element of distraction, and in that way provide a partial "unloading" of the associated disc. The current level of wisdom suggests that both of these would have salutary effects.

The theoretic advantages of a posterior approach are well established. Firstly, and most importantly, this is a far easier technical approach than an anterior approach, and carries with it a substantially less chance of injury to a major vessel or a viscus; above all of that, a posterior approach often is necessary to treat the symptomatic lesion. Secondly, because it can be accomplished in a much shorter period of time, it requires far less anesthesia. Thirdly, the potential complications are significantly less, primarily due to some of the issues elucidated above. Fourthly, such devices as well as the surgical and hospital time for implanting them are far less costly than those associated with an artificial disc. This is obviously an advantage particularly in this day and age. Therefore, it has become apparent, that at least in some instances, it is desirable to achieve a surgical endpoint in which preserving the motion of the involved spinal segment is desired but performing the necessary surgery to accomplish "total disc replacement" is not appropriate.

In order to speak to this particular subset of patients, a number of devices have been recently introduced that can be placed through a posterior (traditional) approach and will preserve motion. Examples of this last strategy would include the posterior motion preserving device marketed by Scientix, as well as the Dynesis system.

The first posterior dynamic stabilization system that seems to have gained modest acceptance is the Scientix, a French company that has accomplished considerable notoriety throughout the spinal surgical world. This system involves a pedicle screw inserted into the superior and inferior vertebrae of a target motion segment, these screws being then connected to each other through a bridging component, which is the main focus of mobility in this device. This bridging piece, from a special design, allows for some flexion, extension, and rotation. The Dynesis System, marketed by Zimmer, offers an even simpler approach to the problem, which basically involves establishing pedicle screws fixation at the superior and inferior vertebra of the target motion segment, then hooking these together with a flexible material.

These systems are designed to be connected to the vertebrae of a target motion segment by pedicle screws. However, rather than the classic pedicle screw construct which involves connecting the pedicle screws to each other with a stabilizing, inflexible rod, these pedicle screws are connected to each other by a device that provides flexibility to the entire system. In the case of the Scientix device, the rod is designed to spin/rotate, as well as have some superior/inferior motion. In the case of the Dynesis system, the connecting device is made of a cord/fabric type material which is obviously flexible.

Yet other embodiments of dynamic stabilization systems have appeared. Recently, a device was introduced by Panjabi that provides a spring device to the ends of the connecting rods. Other devices will probably soon be introduced as well.

One issue that is often a focus of discussion is the role that the disc height contributes to the overall pathology. It is generally agreed upon that this is probably significant in a patient in whom the loss of disc height is associated with foraminal stenosis resulting in radiculopathy corresponding to the nerve root exiting at that level. However, the issues are much less clear in terms of discogenic pain syndromes. While many authors feel that the loss of disc height is associated with back pain, extensive review of the literature fails to demonstrate this to be a universal truth. Moreover, while theories regarding the genesis of such pain abound, none have been completely accepted. One interesting theory that has been alluded to above, and which has begun to gain momentum in recent times, is the possibility that disc height loss is related to ischemic changes in the end plates, which then lead to "discogenic pain syndrome." Which comes first—the ischemic changes or the loss of disc height—is not yet known. But it is clear that in at least a subset of patients, these changes ultimately lead to further disc degeneration resulting in painful discopathy. What has been demonstrated clinically is that in properly selected patients, restoration of disc height with distraction of the associated vertebrae will result in improvement of radicular and/or back pain. Therefore, it seems logical that treatment approaches that are designed to preserve motion should also provide a mechanism by which disc height can be restored and maintained at the restored height level. There is clearly a need for such technology. The device herein disclosed differs from the previous art in several important aspects. Firstly, it can be inserted using a minimally invasive approach. Secondly, the herein disclosed is unique insofar that this device can be adjusted in terms of the amount of flexibility that it provides to the target motion segment. Thirdly, this device can be inserted into the target motion segment or segments and then distraction can be applied, by which disc height can be restored and maintained. Finally, this device can be converted to a classic non-dynamic system in order to encourage the establishment of a fusion in its place. Such a device, and system of implantation, is unique, useful, novel, and non-obvious.

SUMMARY OF THE INVENTION

The primary aspect of this invention to provide a spinal implant device which, once implanted into a target motion segment will preserve/restore the natural motion of that target motion segment; furthermore, at any time after implantation, this device may be re-adjusted in terms of the amount of motion conferred upon the target motion segment, so that the system may ideally recapitulate/restore the natural motion of a target motion segment, even in the face of changing conditions. Additionally, the device can be implanted using a minimally-invasive posterior approach; alternatively, it may also be implanted through a larger or "open" surgical incision.

This device is specifically designed so that once implanted, the system does not intrude upon the facet joints adjacent to the target motion segment. There are yet other objects and goals of the invention disclosed below. Additional devices used for implantation and a system of implantation are also disclosed.

In order to address these issues, the inventor invites the reader to recognize that in terms of body habitus, biomechanics and pathology, broad variation and immense individuality of patients exists. Therefore, it is another object of this invention to provide a spinal implant device and system for use that not only speaks to this range, but offers multiple options to both surgeons and patients in response to this variation. This is done through numerous preferred and alternative embodiments of both the device to be implanted as well as the method of implantation. Furthermore, there may be some embodiments of this invention which are far better suited for some patients, while other embodiments are better suited for implantation into other patients. The two principal embodiments include an embodiment in which the device is fully-assembled or unitized prior to presentation to the operative field and implanted as such. The second principal embodiment, alternatively, is one in which the bone fasteners are initially implanted into the desired location and then the assembly of the device is completed; this is the so-called assembly in situ.

One critical option that this system offers is a variety of constructs, particularly in terms of multi-segment constructs, and may be customized to the specific operative/pathologic anatomy of any particular patient. To that end, this system may permit implantation of a multi-level motion-preservation construct, or a construct that preserves motion at one or more motion segments in combination with a fusion/stabilization construct at other level(s) (i.e. motion preservation at L4-5, in combination with fusion/stabilization at L5-S1); beyond that, any or all segments of this system can be converted from a motion preservation construct to a stabilizing (fusion) construct without removal of the device.

These and other objects of this invention can be achieved by providing a mechanism by which this invention imparts adjustable constrained motion upon a target motion segment(s). Such a mechanism can be achieved by providing a lever in which the resistance or output arm can be varied. In order to understand this mechanism better, a brief review of the physics of levers will be helpful.

DETAILED DESCRIPTION

The invention relates to a spinal implant device that is implanted into either the pedicles or lateral masses of at least a first and a second vertebra. The device comprising at least one target motion segment of the spine, the implantation of the spinal implant device resulting in the creation or restoration of the natural motion of the target motion segment or segments by establishing controlled but adjustable movements of the target vertebrae through their natural range of motion while maintaining the appropriate center of rotation throughout the movement and, in this way, establishing a constrained but adjustable dynamic kinematic relationship between the vertebrae comprising the target motion segment(s).

Furthermore the invention relates to a method of implantation of the spinal implant device bilaterally into the vertebrae of at least one target motion segment in a human spine, using a minimally-invasive technique. First, the patient is placed into the prone, lateral, or any other acceptable position on the operating table. After establishing anesthesia utilizing any acceptable technique, a sterile operating field is created in which the surgical procedure can be performed. Any acceptable manner of intraoperative imaging (e.g. X-ray studies, fluoroscopy, CAT scanning, MRI scanning, computer-generated image guided studies, or any other form of image guidance) is used to identify the location of the target motion segment or segments as well as the relationship of this location to the skin of the patient. A purpose-specific template is used in concert with the aforementioned imaging to determine the entry point on the skin whereupon appropriate skin incisions are created that will provide access to the subsurface target pedicles of a target motion segment or segments.

Figure 8A:
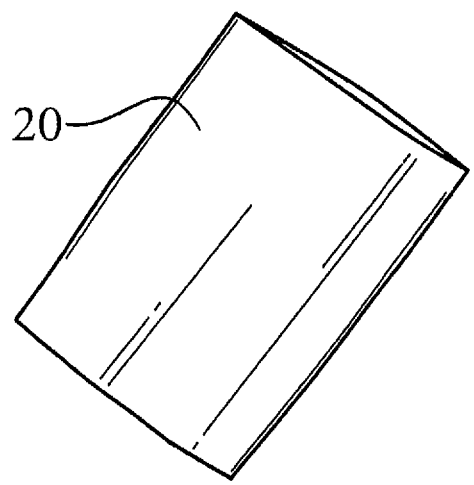
FIG. 8A is a lateral view of the purpose specific retractor used in this surgery.
Figure 8B:
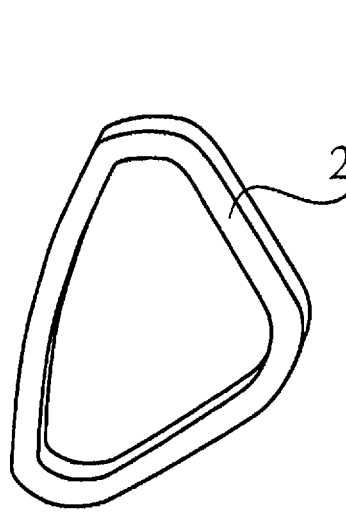
FIG. 8B is an elevational view of the purpose specific retractor used in this surgery.
Figure 8C:
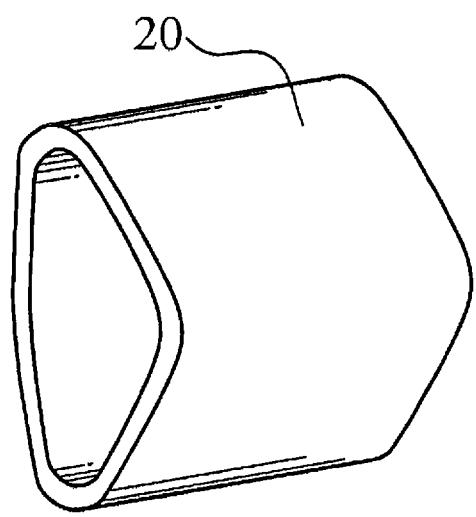
FIG. 8C is a top view of the purpose specific retractor used in this surgery.
Figure 9:
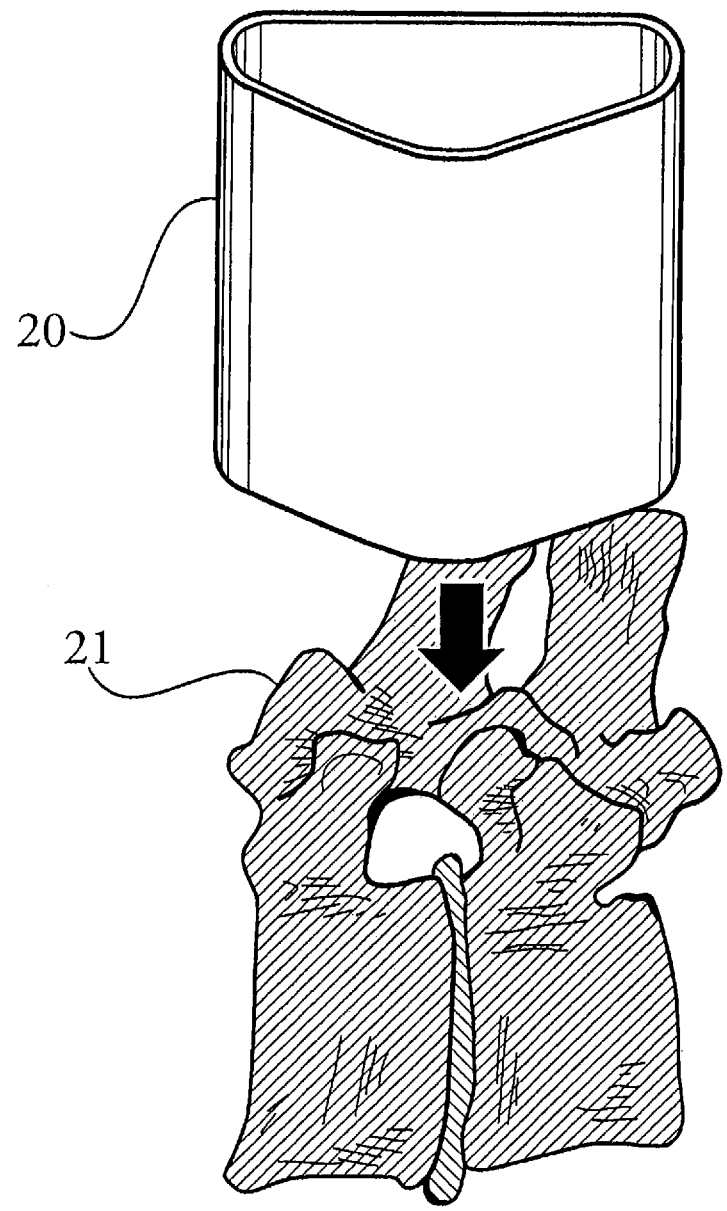
FIG. 9 shows a lateral view of the purpose specific retractor positioned over a target motion segment.

Second, inserting one pedicle trocar for each pedicle and advancing the leading ends of the pedicle trocars until they have entered the base/entry point of the target pedicles. Using the image-guided system, confirming that the pedicle trocars are in an acceptable position at the entry point to the pedicles. Thereafter introducing a purpose-specific retractor in which the cranial and caudal aspects of this retractor (see FIG. 8A, FIG. 8B and FIG. 8C) have been fashioned to recapitulate the geometric configuration of the exterior surface of the pedicle trocars, and advancing this purpose-specific retractor over the pedicle trocars such that they would relate intimately to the exterior surfaces of the pedicle trocars. The retractor may be expanded as necessary so that the retractor provides adequate access to the target area for the insertion of the spinal implant device described herein. Removing the inner trocars of the pedicle trocars, leaving the outer sheath/retractor complex to act as a guide for the passage of a drill and/or tap which is then utilized to create drill holes for placement of the pedical screws which secure the spinal implant device to the target vertebrae followed by removing the outer sheaths of the pedicle trocars.

Figure 10:
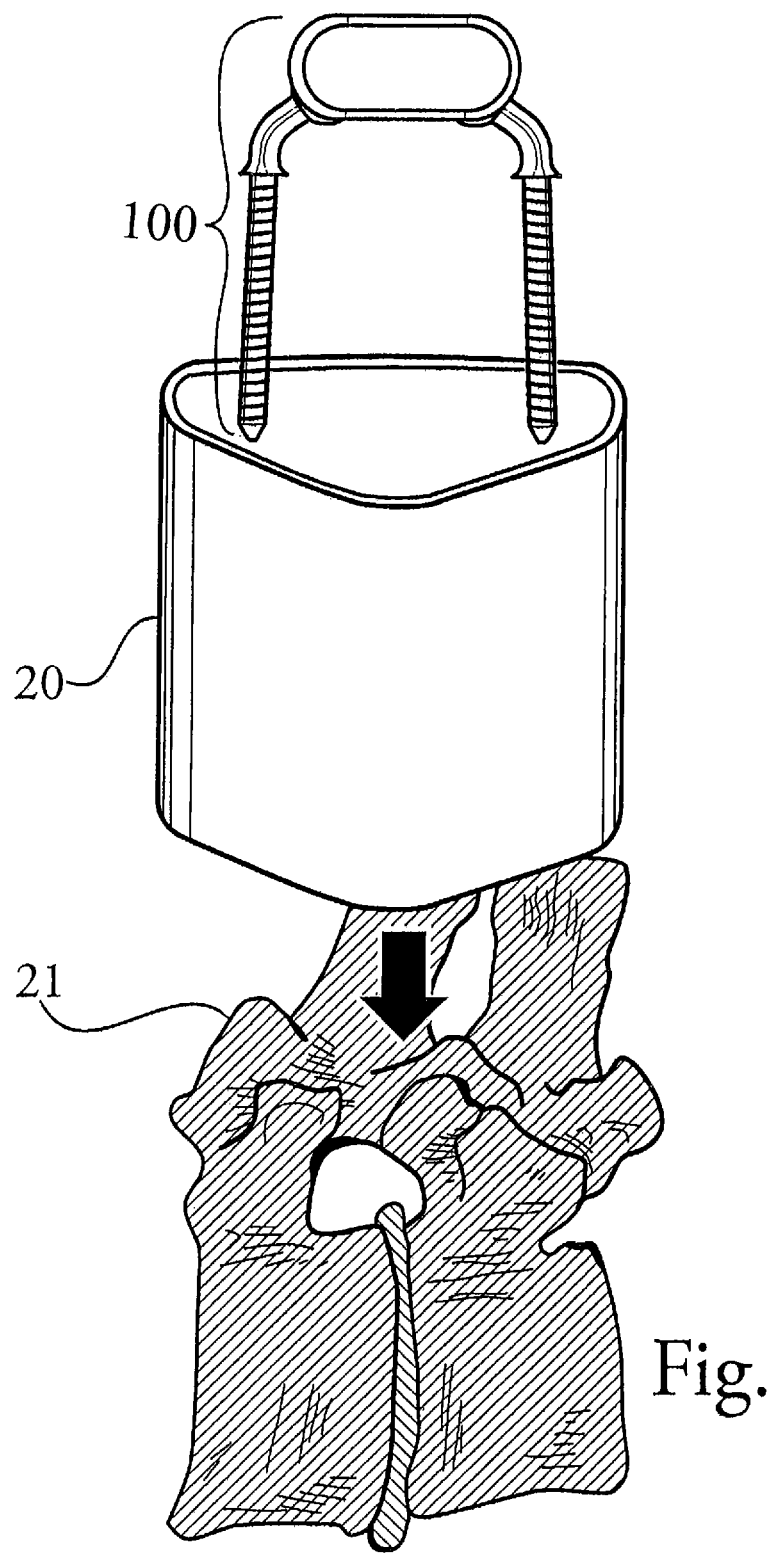
FIG. 10 shows the assembled invention being passed through the purpose specific retractor in anticipation of placement into the target motion segment.
Figure 11:
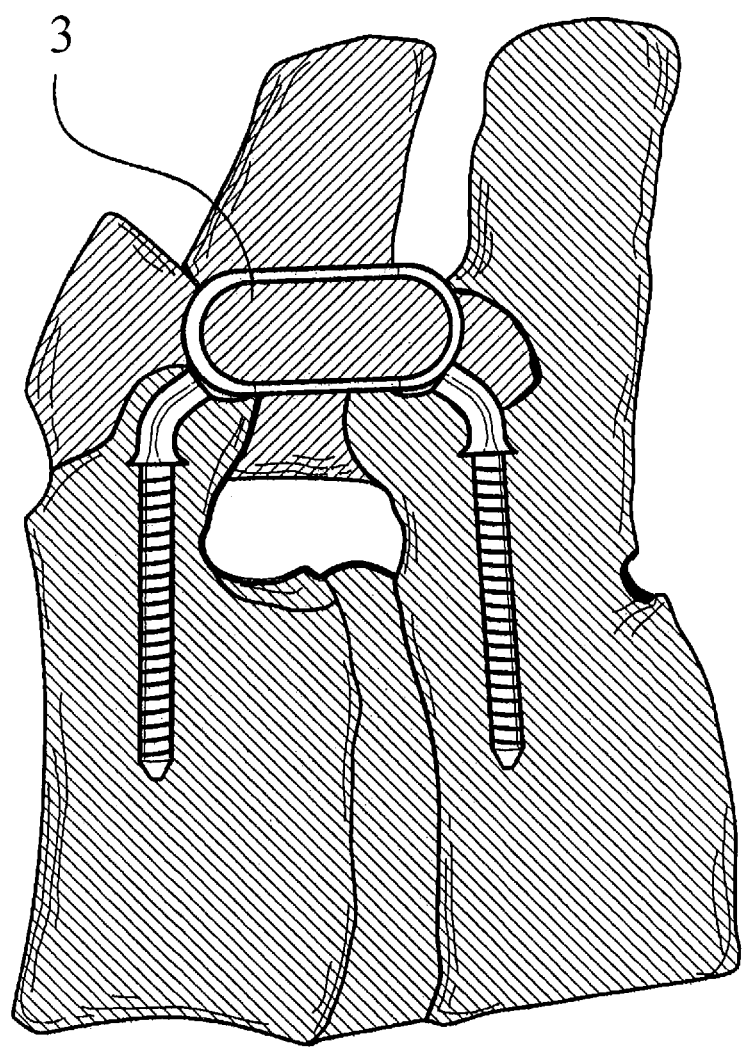
FIG. 11 is a lateral view of the assembled invention that is schematically represented in terms of its position after complete insertion.
Figure 12:
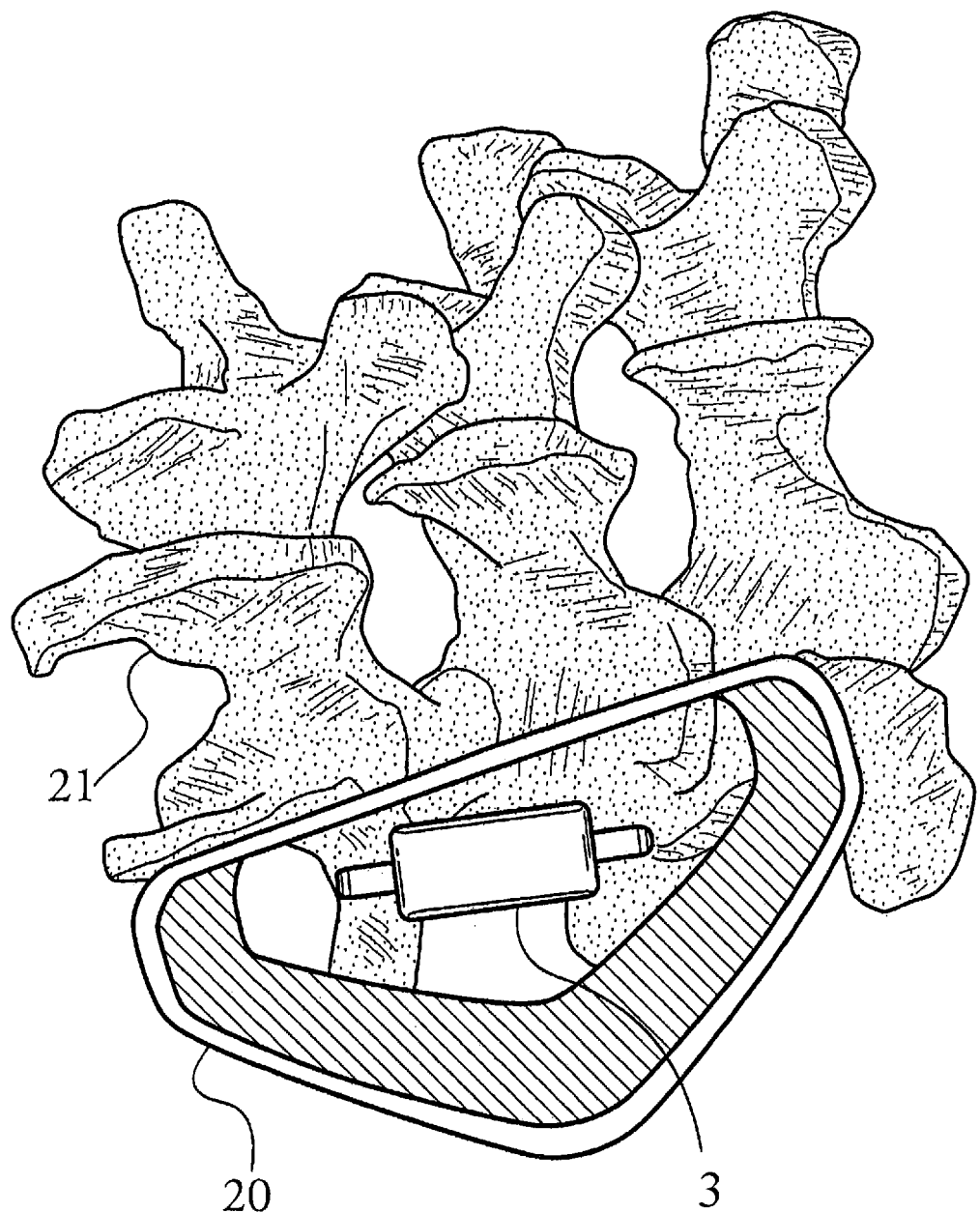
FIG. 12 is a view through the purpose specific retractor with the assembled invention having been implanted in a target motion segment.
Figure 13:
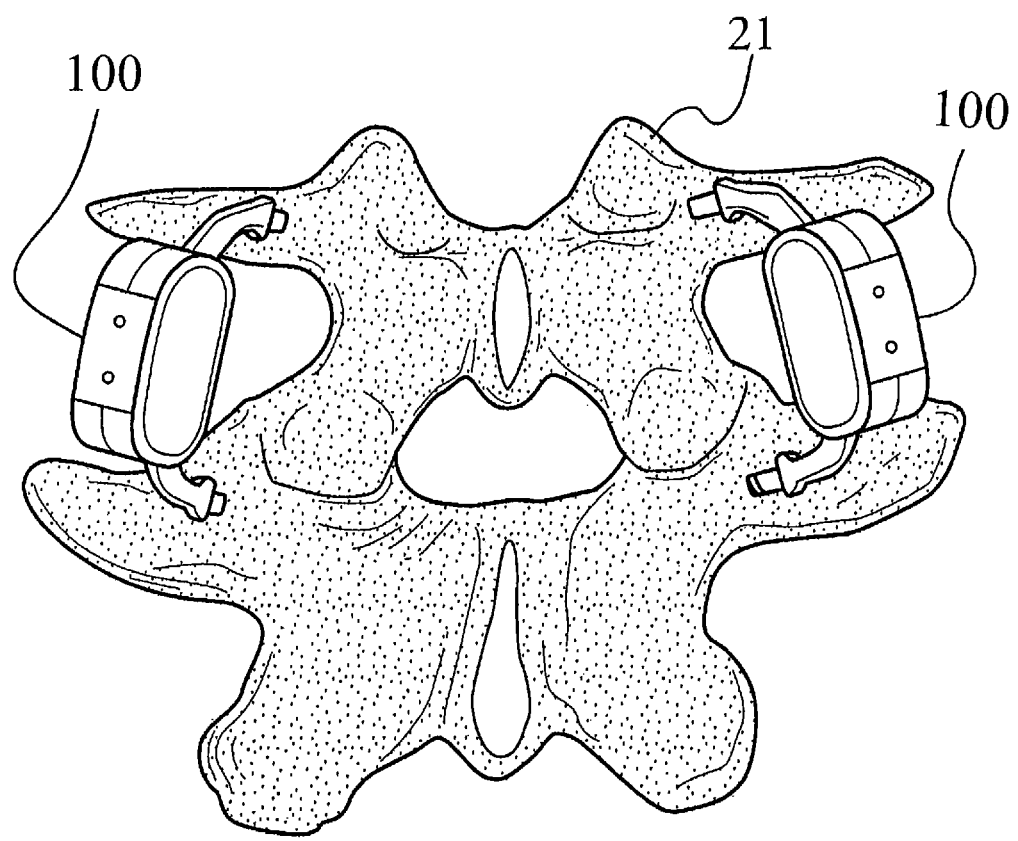
FIG. 13 is a surgeon's view of both assembled inventions having been bilaterally inserted into a target motion segment.
Figure 14:
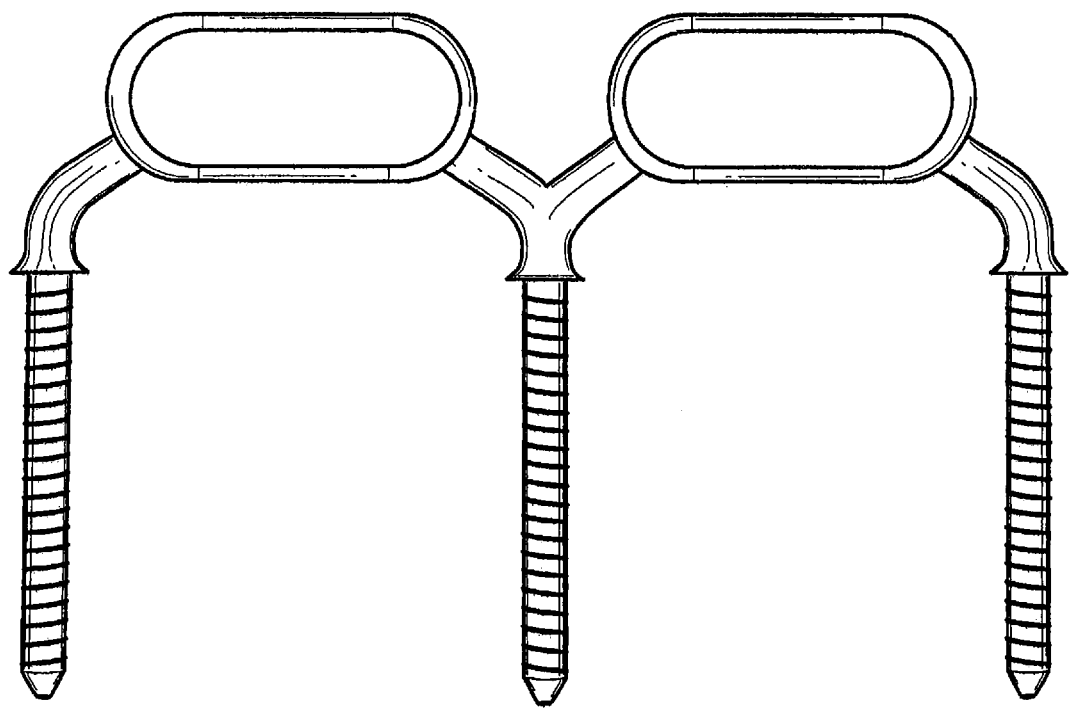
FIG. 14 is a diagonal connector fixed to the lofted chamber.

Using a purpose-specific insertion apparatus to stabilize and insert the spinal implant device and using the retractor 20 as a guide, the fully-assembled/unitized spinal implant device 100 is inserted into the target motion segment 21. See FIG. 10.

Using the flexometer/extensometer to be disclosed below the compliance and degree of instability of the target motion segment is determined.

Filling the chambers of the chamber housing unit of the spinal implant device with a fluid, microspheres, nanospheres, or whatever medium is appropriate to the level as predicted by the data developed from the use of the flexometer/extensometer, and by doing so, creating a lever in which the resistance against the output arm can be variable and adjustable, and then removing the retractor and closing the incision.

Figure 1:
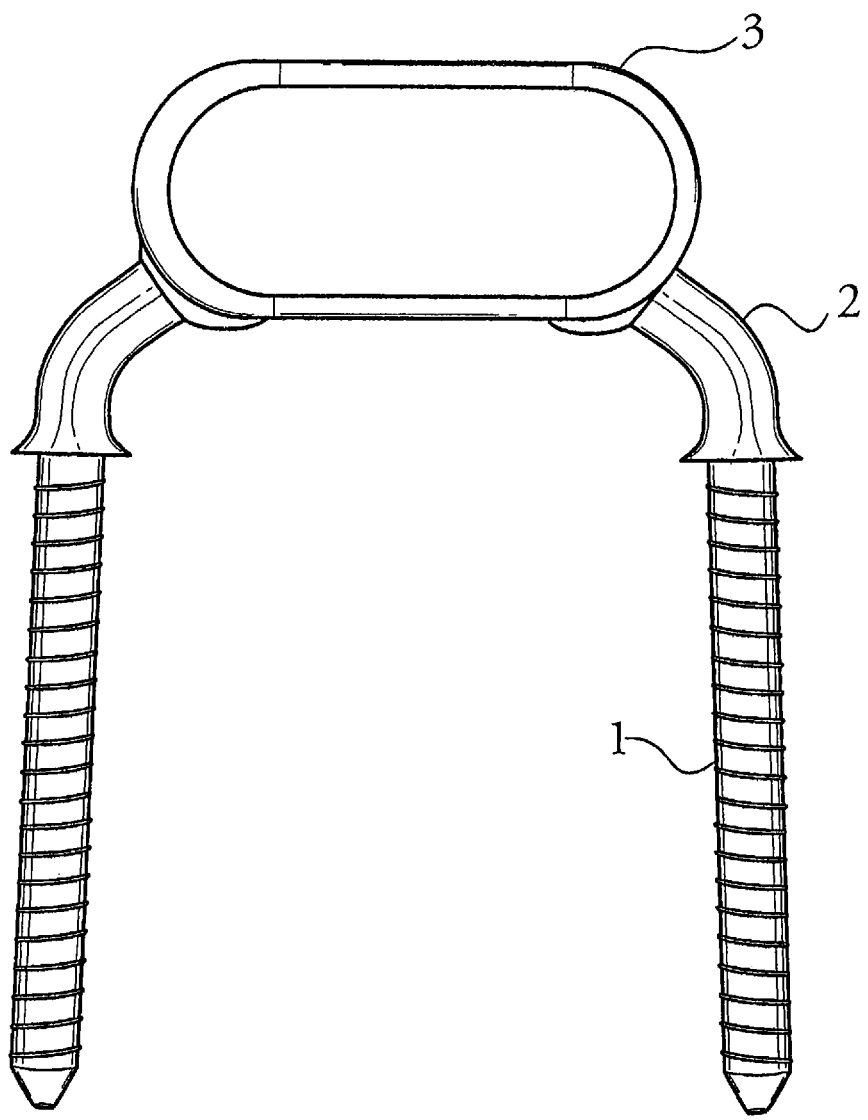
FIG. 1 is a lateral elevational view of the assembled device with the anterior surface of the chamber housing unit cut away.
Figure 2:
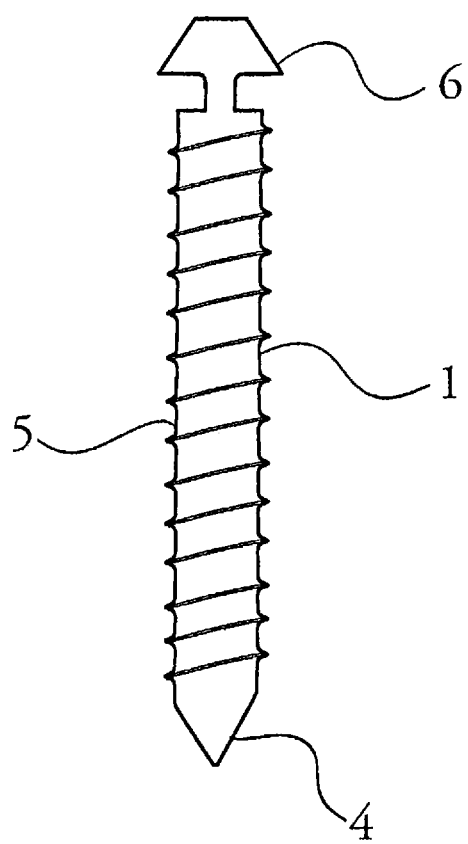
FIG. 2 is a lateral view of the bone fastener.

As shown in FIG. 1, the spinal implant device may comprise at least a pair of pedical screws 1, each of these being irreversibly coupled at their trailing ends with the leading end of a diagonal connector 2 which, in turn, is coupled at its trailing end with a chamber housing unit 3. The pedical screws 1 may be composed of steel, titanium, porcelain, human or vertebrate bone, or any other substance or combination of substances, alloys, or compounds known or acceptable to the art. The pedical screws 1 are specifically configured to be inserted into the pedicles of the target motion segment(s). Referring to FIG. 2, the pedical screws 1 are comprised of a leading end 4 which may configured with sufficient sharpness that this bone fastener is self-tapping/self-drilling. Alternatively, this leading end may require pre-drilling and pre-tapping prior to insertion. The pedical screw 1 is also comprised of a shaft 5, which is threaded with an adequate threading, pitch, sharpness, thread size, and ratio of inner to outer diameter so as to maintain secure fixation within the pedicle. The pedical screw 1 is also provided with a trailing end 6.

The trailing end 6 of the pedical screw 1 can be substantially cylindrical, hemispheric, rhomboidal, spherical or of any other acceptable geometric configuration and which is monolithic with the shaft of the bone fastener by being continuous with the shaft 5 via a somewhat narrowed connecting isthmus and thus providing a configuration by which the trailing end 6 of the pedical screw 1 may be encased within the leading end of the diagonal connector 2, thus creating a unique configuration that results in an irreversible coupling between the leading end of the diagonal connector 2 of the spinal implant device. This configuration provides a unitized embodiment of the spinal implant that is completely assembled prior to implantation, and may be implanted in this fully-assembled configuration into the target motion segment.

The diagonal connector 2 of the spinal implant device may be composed of titanium, polymer or any substance acceptable to the art. The diagonal connector 2 is comprised of a leading end, and is coupled with the trailing end of the pedical screw 1. This diagonal connector 2 is also comprised of a body which is coupled with the chamber housing unit 3 and a trailing end.

The leading end of the diagonal connector 2 which is known as the lofted chamber and is a solid frame with a central chamber 17. This chamber is specifically configured to encase the trailing end 6 of the pedical screw 1. The leading-most end of the diagonal connector is provided with a shelf 10; ledge, or similar configuration which serves to encase the trailing end 6 of the pedical screw 1 and in that way create an irreversible coupling between the pedical screw 1 and the diagonal connector 2.

The irreversible coupling of the trailing end of the pedical screw 1 with the diagonal connector 2 results from a configuration in which both of these have been provided with corrugations/crenellations on any combination of apposing surfaces, such as the undersurface or base of the of the trailing end of the bone fastener and the corresponding surface of the ledge/shelf of the diagonal connector 2. Alternatively, on the trailing end of the shaft 5 of the pedical screw 1 and the corresponding surface of the shelf of the lofted chamber, or any conceivable combination of the above, this configuration resulting in an interface of the corrugations/crenellations such that upon securing the pedical screw 1 into position within the pedicle the comtgation/crenellation mechanism is deployed resulting in locking of the coupling between the pedical screw 1 and the diagonal connector 2, thus creating a configuration by which the pedical screw 1 and the diagonal connector 2 function as a single unit.

The trailing end 6 of the pedical screw 1, which is provided with a flattened area known as the insertion surface and which has been specifically configured to accommodate the leading end of a screw driver, a Philips-head type configuration, a Hex-wrench, or any other type of insertion device acceptable to the art.

Figure 3:
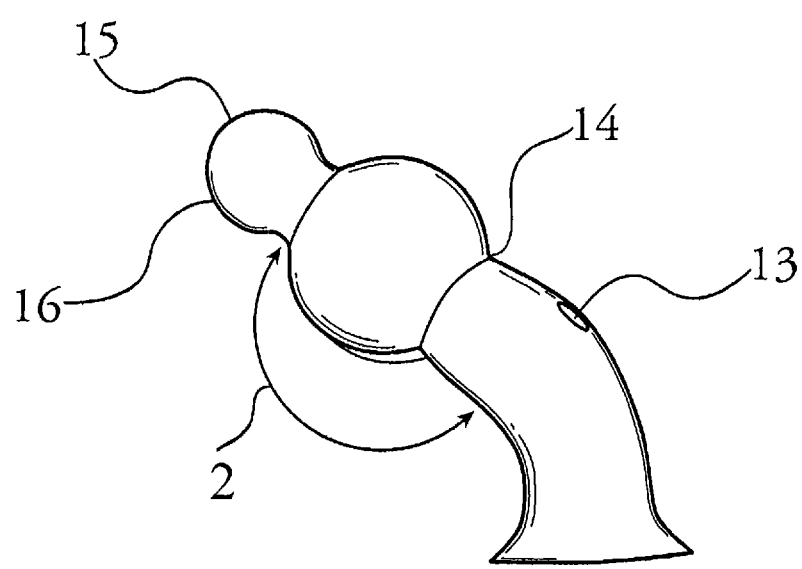
FIG. 3 is a lateral view of the diagonal connector.
Figure 4:
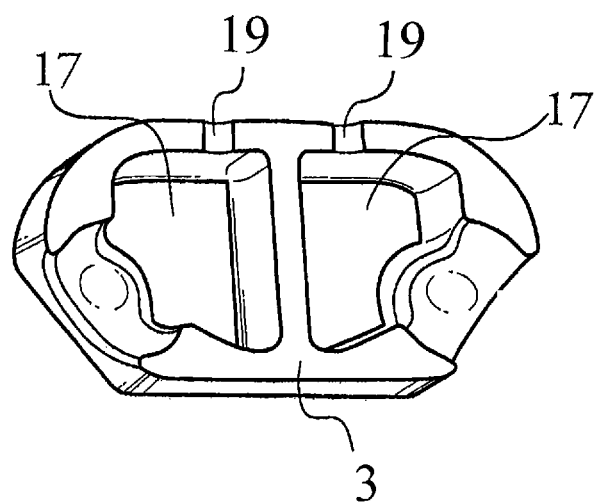
FIG. 4 is a lateral elevational view of the fluid chamber housing unit with the anterior surface cut away.
Figure 5:
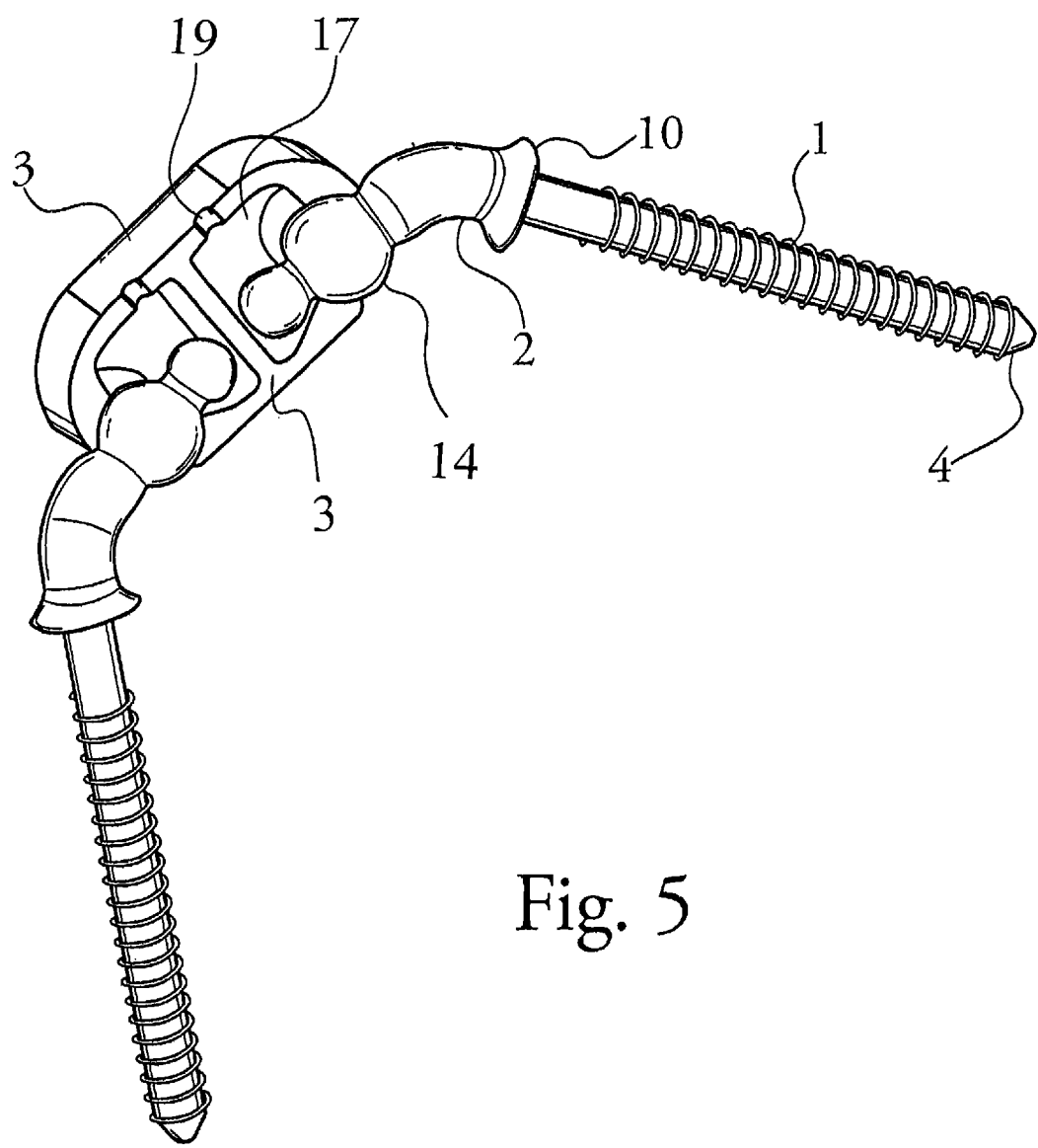
FIG. 5 is a lateral view of the coupling of the trailing end of the bone fastener within the lofted chamber, wherein the front surface has been cut away to demonstrate the coupling mechanism.

As shown in FIG. 3 the dorsal surface of the diagonal connector 2 is provided with an aperture 13, also known as the access window, through which the leading end of any insertion device achieves access to the insertion surface.

The body of the diagonal connector 2 in the spinal implant extends from the lofted chamber to the trailing end of the diagonal connector 2 and is directed posteriorly towards the chamber housing unit 3 as well as towards the other diagonal connector associated with this target motion segment, and coupling in a unique fashion with the chamber housing unit as the result of a substantially spherical enlargement 14 of the body of the diagonal connector, this enlargement being encased within a socket which comprises at least a part of the wall of the chamber housing unit 3 to form a dampening sphere 16 between the trailing end of the diagonal connector 2 and the leading end 15 thereof.

The trailing end of the diagonal connector 2, which may be spherical in configuration and known as the dampening sphere 16, and which, in the fully assembled spinal implant device 100 is disposed within the fluid containing chamber 17 of the fluid chamber housing unit 3.

The fluid chamber housing unit 3, for which there is a chamber housing unit bilaterally arranged for each motion segment being created, couples with the dampening spheres 16 of the bodies of the diagonal connectors 2. This chamber housing unit 3 may be made of titanium, polymer or any other substance acceptable to the art and is comprised substantially of an ovoid configuration that contains two chambers 17 each of which houses the dampening sphere 16 of a diagonal connector 2 to which a corresponding chamber 17 is coupled.

The chambers 17 of the fluid chamber housing unit 3 may be a singular chamber or may contain multiple sub-chambers within any particular chamber, and may or may not be lined with a flexible substance such as polyester, polysulfone, or any other such substance acceptable to the art. This lining is intended to enclose and contain a fluid medium which has been instilled into the chamber housing unit.

The exterior of the fluid chamber housing unit 3 is provided with an access port 19. This access port 19 being provided with a diaphragm composed of a perforatable substance such as polyester, polysulfone, polyamide, or any other substance acceptable to the art, and which provides repeated access to the chambers 17 of the chamber housing unit 3 and serves as the site through which the constraining medium is instilled therein. Other port means such as replaceable plugs may be used as well.

Figure 15:
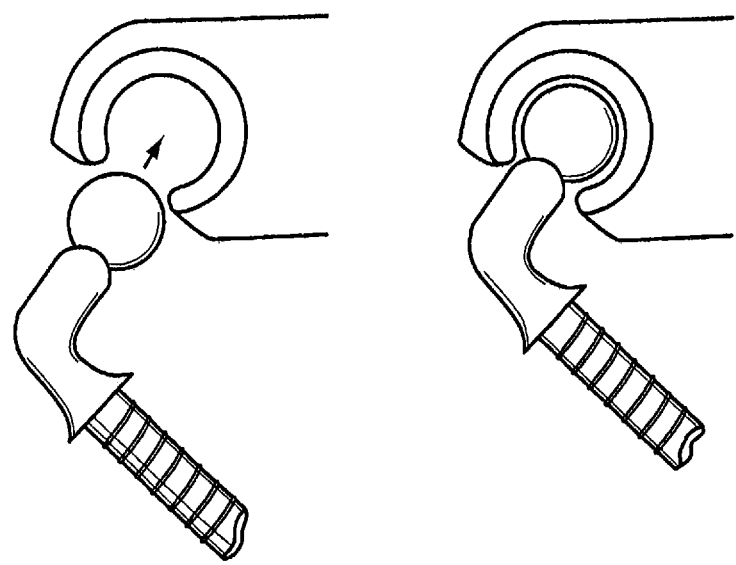
FIG. 15 is an alternative embodiment with an insertable pivot sphere.

An alternative embodiment of the spinal implant device is shown in FIG. 15 in which the device may be assembled in situ rather than implanted fully assembled. As such the pedical screws 1 are initially implanted, being then coupled with the diagonal connectors 2 which are in turn coupled with the chamber housing unit 3. Furthermore any combination of elements (i.e. unitized pedical screw 1 and diagonal connector 2 which is then coupled with the chamber housing unit 3 or, alternatively, unitized diagonal connectors 2 and chamber housing unit 3 which are then coupled with the pedical screws 1) may be combined in assembling the spinal implant device. The coupling may result from a pressure fit, use of securing screws, bolts, nuts or any other mechanism for securing the joint between components of prosthetic hardware acceptable to the art; such coupling may occur at any point in the construct.

An alternative embodiment of the leading end of the pedical screw 1 that is specifically configured to couple with an alternative embodiment of the pedicle trocar in which the leading end of the pedicle trocar is modular in configuration and designed to be introduced into the pedicle and retained within the pedicle after removal of the remainder of the pedicle trocar, the modular leading end of the pedicle then irreversibly coupling with the leading end of the bone fastener which is blunted with a central hollow core which is fashioned to couple with the trailing end of an alternative embodiment of the pedicle trocar.

The pedicle trocar is comprised of an inner trocar and an outer sheath, each of which are comprised of a leading end, a shaft and a trailing end. The inner trocar has a leading end that has been provided with sufficient sharpness to readily perforate the bony cortical surface of the entry point to the pedicle and be advanced into the pedicle, this leading end being composed of steel, titanium, or any other metal acceptable to the art, and specifically being composed of a substance that is radiopaque and therefore easily identified using image-guided studies, in contrast to the shaft and trailing end of the inner trocar.

The outer sheath of the pedicle trocar is composed of any radiolucent substance acceptable to the art, and which has an external surface that recapitulates the configuration of the inner surface of the cranial or caudal ends of the retractor 20. The retractor 20 is substantially triangular in configuration as viewed from the top view, and is composed of multiple walls that are joined by multiple expandable chambers which may be filled with any fluid medium in order to be expanded to the appropriate size and configuration to provide adequate access to the target motion segment(s).

The cranial and caudal aspects of the retractors 20 in which the inner surfaces are configured to recapitulate the configuration of the external surface of the outer sheath of the pedicle trocars.

Figure 16:
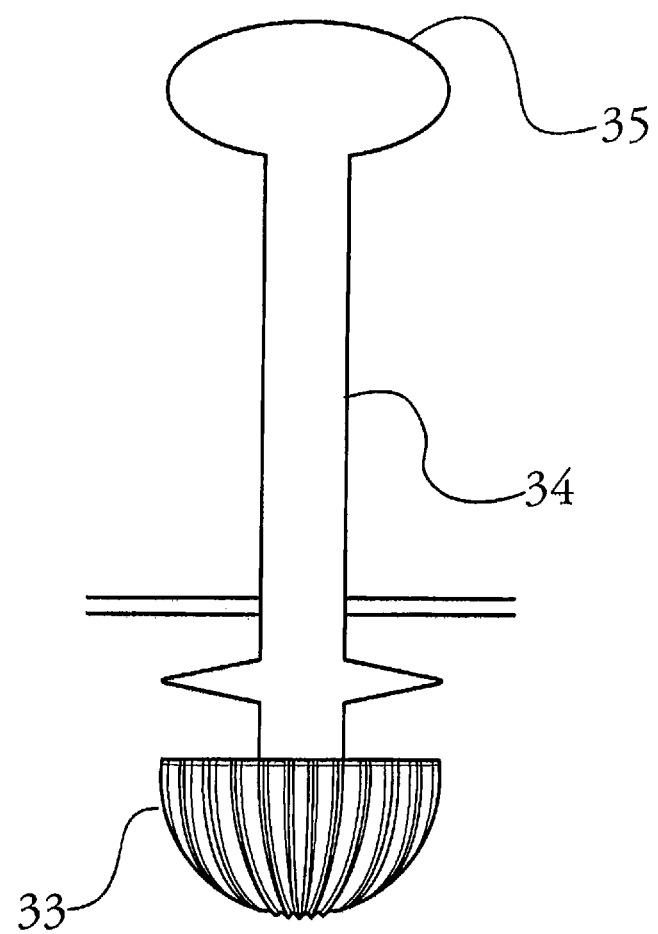
FIG. 16 is a schematic representation of the insertion device.
Figure 17:
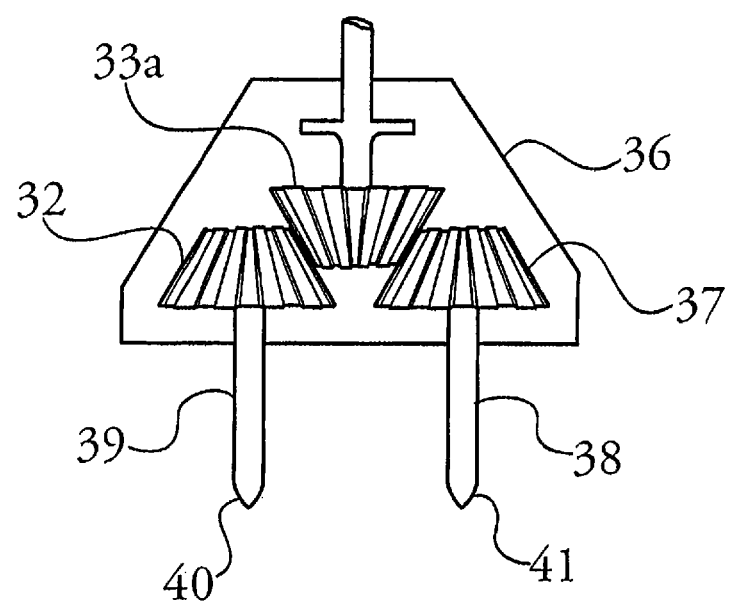
FIG. 17 is a schematic representation of the insertion device in operation.
Figure 18:
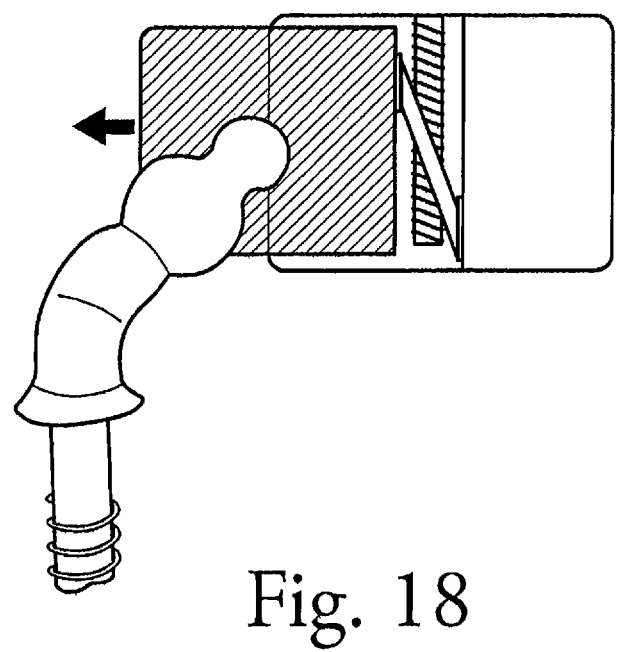
FIG. 18 is an expandable fluid chamber housing unit.
Figure 19:
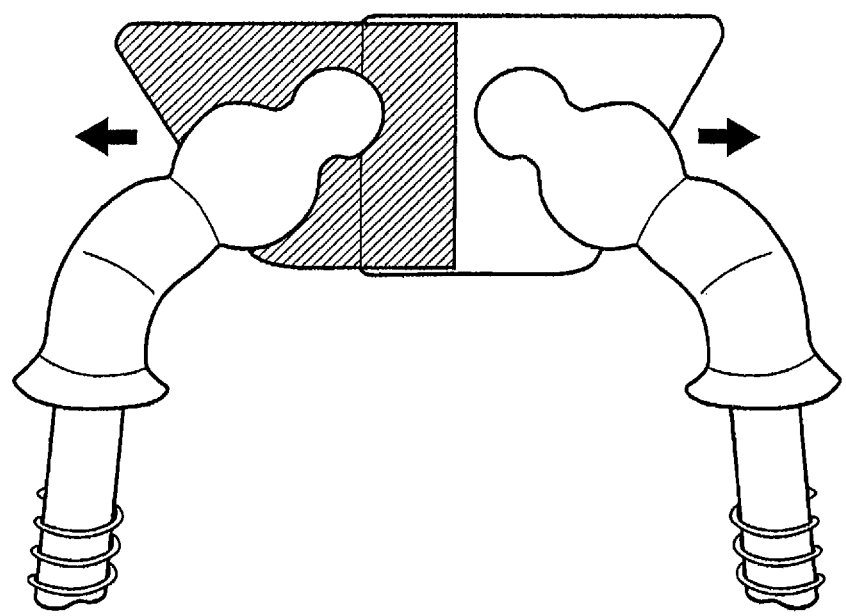
FIG. 19 is a mechanically expandable fluid housing chamber unit.

Referring to FIG. 16, the apparatus is configured to implant the spinal implant device by inserting a pair of leading ends, a body, and a trailing end. The trailing end of the insertion apparatus is configured to provide a handle 35 of any acceptable geometric configuration, be it a round handle, a T-handle, or any other geometric configuration. Additionally, the apparatus is provided with a shaft 34, and a trailing end 33 which is either monolithic or coupled to the handle 35. The shaft 34 extends into the body of the insertion apparatus whereupon the leading end of the shaft is coupled with a beveled gear 33a (see FIG. 17) in such a fashion that rotation of the handle 35 at the trailing end of the insertion apparatus results in actuation of the beveled gears.

The body of the insertion apparatus comprises an outer frame 36, encasing an interior mechanism. The leading end of the shaft extends from the trailing end of the insertion apparatus and is received into the body. The pair of shafts 38, 39 constituting the leading ends of the insertion apparatus arise from the body. The interior mechanism of the body of the insertion apparatus comprises the leading end of the shaft, a series of gears 32, 33a, 37 which interface with each other, and the trailing ends of the pair of shafts and constitute the leading ends of the insertion apparatus. The outer frame 36 of the body of the insertion apparatus may have an outer covering consisting of an encasement which completely covers the interior mechanism. Additionally, this outer covering is provided with suitable openings through which the aforementioned shafts may pass. The outer covering is provided with a clip or stabilizing frame that arises from the ventral surface of the body of the insertion apparatus, the clip or stabilizing frame arising from the outer frame between the apertures through which the uppermost portions of the pair of shafts that comprise the leading ends of the insertion apparatus. The clip or stabilizing frame being provided to stabilize the chamber housing unit 3 against the insertion apparatus during the process of implanting the spinal implant device.

A pair of additional beveled gears 32, 37 which are components of the interior mechanism engage the beveled gear 33a found at the leading end of the shaft. Rotation of the handle 35 results in rotation of the beveled gear 33a, this rotation being ultimately translated to this pair of beveled gears 32, 37, which are monolithic with or coupled to the trailing ends of a pair of shafts 38,39. These shafts represent the leading ends of the insertion apparatus and extend for an unspecified length with the leading ends 40, 41 fashioned into a Philips head screwdriver, a straight screwdriver, a Hex-shaped screwdriver, or any other configuration so as to couple with the insertion surfaces of the trailing ends of the pedical screws 1.

The operation of the device employs simple hydrodynamics and simple lever mechanisms. A lever is defined as a rigid bar that turns about an axis of rotation or fulcrum (A). Two opposing forces then act on this rigid bar resulting in this movement: A Motive Force (F) is an effort or exertion applied against one aspect of the lever which results in movement of the lever, typically against a weight or resistance known as a Resistive Force (R). The Motive Force is also referred to as the input arm or effort; the Resistive/resistance may be referred to as the output arm or load. A lever is one of the six simple machines defined in physics.

The theory of operation of a lever states that the principle of leverage can be derived using Newton's laws of motion and statics. For example, it can be recognized that to use a lever to lift a certain amount of weight (resistance) with a force equal to half the weight (input), the distance from the fulcrum to the spot where the force is applied must be twice the distance between the weight and the fulcrum. Hence it can be appreciated that the principle consideration predicting the behavior of a lever are the magnitude of the force versus the magnitude of the resistance, as well as the distance from the fulcrum to the application of each of these forces.

In general, the following equation will predict the static equilibrium of a lever system: F1 D1=F2 D2 Where $F_1$ is the resistance or output load; D1 is the distance from the fulcrum to the point where resistance is being applied; F2 is the force or input effort; D2 is the distance from the fulcrum to the point where the force is being applied It can be appreciated from this equation that the distance from either the force or the resistance to the fulcrum also becomes a critical factor in achieving equilibrium. The expression "lever arm," refers to such a distance.

Furthermore, when a moment arm is developed with movement around the fulcrum, then $$Fb=a/bF_a$$

Where
a represents the distance from the fulcrum to the site of the application of force
b represents the distance from the fulcrum to the site of resistance
$F_b$ represents the output
$F_a$ represents the input There are three classes of levers which represent variations in the location of the fulcrum with respect to the Force or input and the Resistance or output. In a first-class lever, the fulcrum is located between the input effort and the output load. In operation, a force is applied (pushing, pulling, applying weight, etc.) to one section of the bar, causing the bar to swing about the fulcrum and overcome the resistance load applied to the other end of the lever.

A second-class lever positions the fulcrum at one end of the bar and the input effort is located at the other end, with the resistance output load at a point in between. In a third-class lever, the resistance is at one end with the fulcrum at the other and the force in between.

A first-class lever comprises a central component of the mechanism of this invention. This is, accordingly, provided with an input arm to which force is applied, an output arm to which resistance is applied, and a fulcrum positioned between these two opposing forces. The input arm of this lever arm is, in fact, a pedicle screw that has been placed into one of the vertebrae of the target motion segment. There is a unique arrangement by which trailing end 6 of the pedicle screw is then irreversibly coupled with the diagonal connector 2. The diagonal connector 2 is then coupled with the wall of a closed chamber 17. This chamber is one of a pair of chambers 17 contained within the chamber housing unit 3. The fulcrum is the coupling of the diagonal connector 2 with the chamber housing unit. The trailing end of the diagonal connector 2 is contained within this (closed) chamber. Because of the irreversible coupling of the diagonal connector 2 to the trailing end 6 of the pedicle screw 1, a force applied against the trailing end of the diagonal connector 2 represents the output arm or resistance of the lever arm. This complex, then, satisfies the general definition of a lever insofar that opposing forces are being applied to each end of this unitized structure. The fulcrum (coupling of the diagonal connector 2 to the chamber housing unit 3) is positioned between the two forces.

The input arm of the lever is thereby translating the movements (force)—normal and abnormal—of the vertebra through the fulcrum (coupling of the diagonal connector 2 to the chamber housing unit) to the output arm of the lever (The resistance created by the closed chamber against the trailing end of the diagonal connector 2). This translation of movement creates a moment arm across the lever. Again, referring to the equations above, it is recognized that any mechanism that affects the resistance applied to the lever arm will ultimately affect the entire system. Since the resistance within the chamber can be varied, the equilibrium of the entire system can be therefore varied. An analogy can be drawn to a simple "see-saw" in which the weights of the participants can be varied, resulting in differing outputs.

The manner by which this invention varies resistance of the output arm of the lever is based on fluid dynamics, and the interplay of fluid dynamics with the output arm of the lever. This interplay will ultimately result in an alteration of the moment arm of the lever, which will, in turn, reflect (in a reciprocal fashion) on the input arm of the lever—in other words, the pedicle screw, thereby altering the movements of the target vertebra. As the chamber housing unit 3 houses the trailing ends of the diagonal components of two adjacent target vertebrae comprising a target motion segment, the lever arms associated with each vertebra within the motion segment will independently translate the movements of the respective vertebra. However, the monolithic frame of the chamber housing unit 3 will then equilibrate and hence stabilize the two and in that fashion stabilize the motion segment as a whole.

Again, when the system is in motion and a moment arm of the lever is developing, this moment arm can be changed again by altering the output aim or resistance, which is located within the central mechanism of the device. This is accomplished through Fluid Dynamics, which shall also be reviewed below.

Therefore, the mechanism is based to a large degree on the physics/behavior of the constraining fluid, and the interaction between the fluid and the output arm moving through it. The science of studying the behavior of fluids is known as "fluid mechanics," and is divided into the science of studying fluids in motion (Fluid Dynamics) as well as at rest (Fluid Statics). In order to better understand this mechanism, therefore, a cursory review of some essential principles of fluid dynamics/mechanics is in order.

Fluids are divided into two broad categories: "Newtonian fluids" (i.e. water, milk, or other "classic" fluids) and their counterpart "Non-Newtonian fluids." These categories generally defined by a very important property of fluids known as viscosity. Viscosity is often thought of as reflecting a fluid's density, which is in fact a different physical characteristic. It is sometimes (in unsophisticated circles) referred to as a fluid's "thickness," and although "thicker," fluids (i.e. motor oil) do (generally) have a higher viscosity, this term actually represents a complex relationship between a fluid's physical characteristics and its flow characteristics. In scientific/mathematic terms, viscosity refers to the flow characteristics of a fluid and is defined as the constant of proportionality between the shear stress and the velocity gradient. This can be represented by the formula:

$$G = -m(du/dk)$$

Where

G is the shear stress exerted by the fluid ("drag")

m is the fluid viscosity (A constant proportionality for any given fluid)

du/dk is the velocity gradient perpendicular to the direction of shear

When a fluid fits this mathematic definition, it is said to be a Newtonian fluid. In practical terms, this equation defines this category of fluids by stating that regardless of the forces acting upon these fluids, they continue to flow. In other words, regardless of how much stirring, mixing, or other physical agitation one applies to a Newtonian fluid (such as water) it will continue to display fluid characteristics.

This is in contrast to Non-Newtonian fluids. This (mathematical) category of fluids does not maintain the same viscosity with an applied strain rate. A classic example of such a fluid is pudding. As this substance is stirred (Application of mechanical agitation) it can actually change its viscosity—in the instance of pudding it can liquefy quite a bit.

The viscosity of Newtonian fluids is dependent only upon temperature and pressure. If the fluid is incompressible and the viscosity is constant across the fluid, the equation governing the shear stress is as follows:

$$Gij = m\left(\frac{dui}{dkj} + \frac{duj}{dki}\right)$$

where

Gij is the shear stress on the face of a fluid element in the jth direction u i is the velocity on the ith direction k j is the jth direction coordinate When an incompressible fluid does not obey this relation, it is a non-Newtonian fluid. The manner by which a fluid resists an object moving through it is intimately intertwined with that particular fluid's flow characteristics—in other words, the fluid's viscosity. A functional example of this is passing a stirring spoon through water and then attempting to pass the same spoon through oil—based paint. The difference is readily apparent.

Hence, it can be assumed that relating to its own viscosity each fluid has a specific resistance to movement of an object passing through that fluid. Furthermore, if that fluid is contained within a closed chamber system, then the resistance to an object passing through that system can be affected principally by three factors: the viscosity of the fluid, the volume of fluid placed into the chamber with respect to the entire volume of the chamber, and whether the fluid is a Newtonian or a Non-Newtonian fluid.

Intuitively, therefore, an extremely viscous Newtonian fluid which only partially fills such a closed chamber may dampen or restrict the movement of an object (i.e. the output arm) passing through that chamber more substantially than completely filling the chamber with a fluid of lower viscosity. Alternatively, a non-Newtonian fluid may not act in a predictable fashion, making non-Newtonian fluids somewhat suboptimal when considered for use in this invention. It should be noted that although it may appear somewhat paradoxical, the inventor anticipates that there may be a major role for microspheres/nanospheres in this technology, despite the fact that they are likely to be considered Non-Newtonian fluids by the mathematical model. Obviously, identifying which fluids will best fit this model may ultimately have to be determined empirically. However, the aforementioned equations and other scientific facts about the behavior of fluids, in combination with the theory of operation of a lever, provide mathematic support of the theoretic basis for this invention.

As shown in FIG. 1 in an embodiment, the invention herein disclosed is configured so as to be inserted in a complete, unitized fashion, with the device fully assembled prior to implantation. This embodiment is comprised of the three components previously disclosed, namely at least a pair of pedicle screws 1, at least a pair of diagonal connectors 2, and at least one lofted chamber housing unit 3. As stated, these components are irreversibly coupled to each other prior to insertion.

The device is anchored to the target motion segment by the use of pedicle screws that are passed into the pedicles of the superior and inferior target vertebrae bilaterally. Therefore a minimum of two pedicle screws (per side) are necessary for a single level construct. It is recognized that in almost all instances, devices would be implanted bilaterally. Ergo, it must be recognized from this point forward that although descriptions of the device will explicitly refer to a single device, such devices would (almost always) be implanted bilaterally in patients suffering from spine disease. This application also discloses embodiments which are designed to enable surgeons to achieve a multi-level construct. In such a construct, three pedicle screws (per side) are needed for a two-level construct, and four screws (per side) would be required for a three-level construct. Such constructs would also be provided with one chamber housing unit per motion segment.

Referring to FIG. 2, the screws 1, consist of a leading end 4, a shaft 5, and a trailing end 6. The leading end 4 of the pedical screw 1 is provided with sufficient sharpness and strength so as to penetrate bone and obtain an adequate purchase within the target bony areas. The pedical screw 1 may have sufficient sharpness and strength so that neither "drilling" nor "tapping" are necessary in the implantation of these pedical screws 1. Alternatively the surgical technique described above actually incorporates "drilling" but not "tapping," as there is an advantage to passing a thin drill insofar that this provides the surgeon with an opportunity to reassess the entry points and trajectories with respect to the target pedicles. Any combination thereof is incorporated in the spirit and scope of this application.

It is anticipated that the pedical screws 1 are composed of a standard surgical metal or alloy such as titanium or stainless steel. However, any alternative metal, metal-like substance, as well as porcelain, bone, plastic, polymer, or any other substance known or acceptable to the art may be used to create the pedical screws 1.

The trailing end 6 of the screw is unique in several respects, and shall hereinafter be referred to as the cylindrical head. The cylindrical head, in the preferred embodiment, is substantially cylindrical in shape with a rhomboidal profile as seen in the lateral view, being tapered such that the trailing end is somewhat smaller in diameter compared to leading end of the cylindrical head, known hereinafter as the base of the cylindrical head, both of which are flattened. Obviously, other geometric configurations such as a spherical or any other configuration acceptable to the art would be included within the spirit and scope of this application. See FIGS. 6B, 6C, 6D and 6E. The trailing end, hereinafter known as the insertion surface of the cylindrical head, serves to receive the leading end of an insertion device (i.e. screwdriver, Philips-Head, etc.). The cylindrical head is monolithic with and articulates to the trailing end of the shaft of the screw via a connecting isthmus that extends between the trailing end of the shaft and the base of the cylindrical head. The configuration created by the isthmus contributes to the irreversible coupling of the leading end of the diagonal connector 2 with the trailing end of the screw, inasmuch as the base of the cylindrical head is expanded, and this additional diameter creates an overhang configured to interface with a component of the leading end of the diagonal connector 2.

Figure 6A:
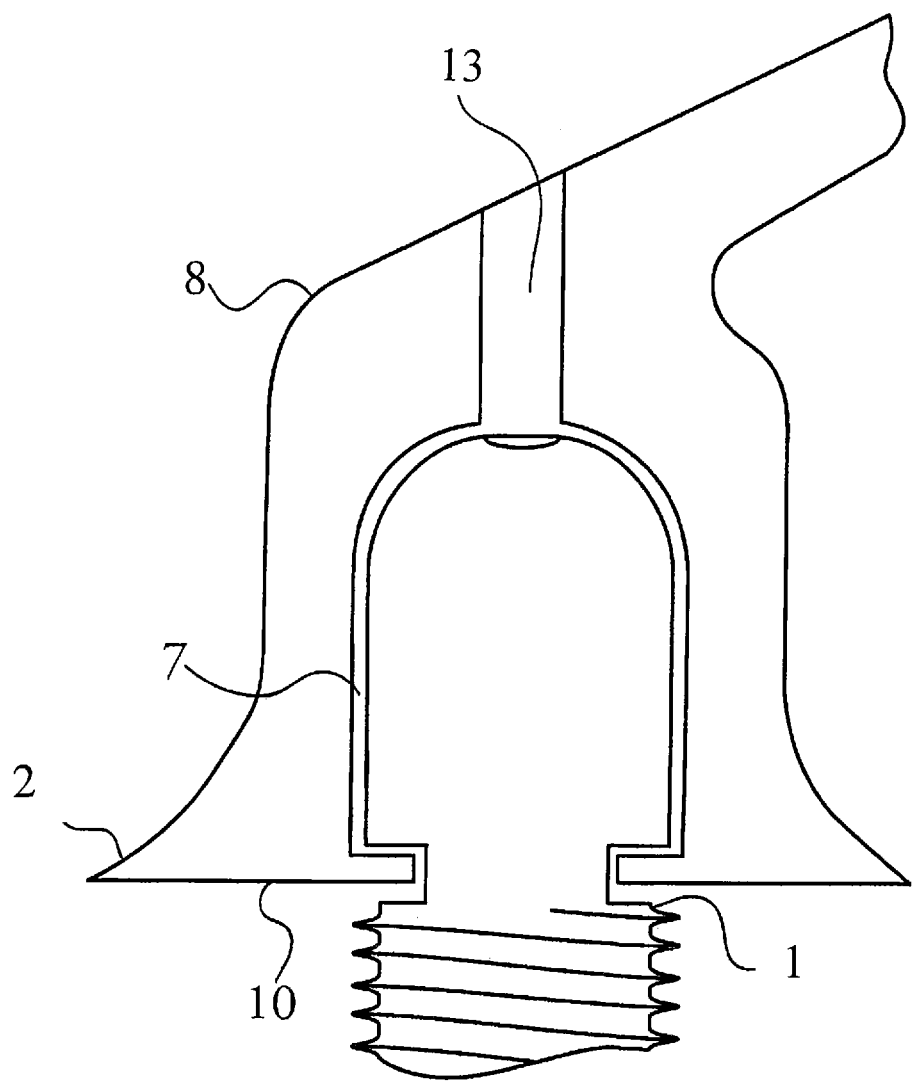
FIG. 6A is a transaxial or top view of the base of the cylindrical head.
Figure 6B:
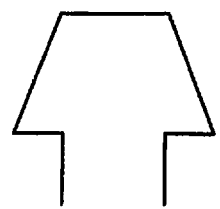
FIG. 6B is an elevational view of the trailing end of the screw demonstrating crenellations at the base of the cylindrical head.
Figure 6C:
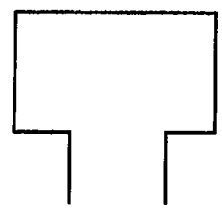
FIG. 6C is an elevational view of the lofted chamber with the front surface cut away, demonstrating crenellations of the inner surface of the horizontal extensions.
Figure 6D:
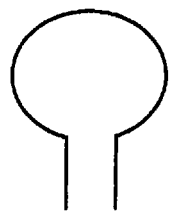
FIG. 6D is an elevational view of the lofted chamber demonstrating and alternative embodiment of the outer surface of the horizontal extensions of the lofted chamber.
Figure 6E:
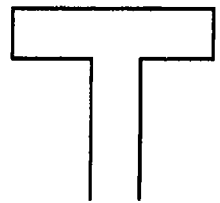
FIG. 6E is an elevational view of the trailing end of the bone fastener demonstrating an alternative embodiment of the trailing end of the shaft.
Figure 7A:
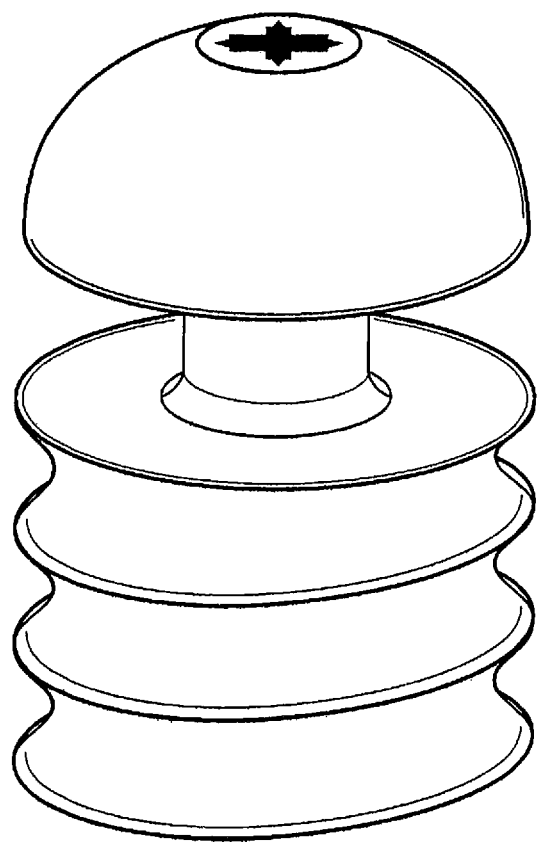
FIG. 7A a lateral cut away view of the preferred mechanism of coupling between the trailing end of the screw and the lofted chamber.
Figure 7B:
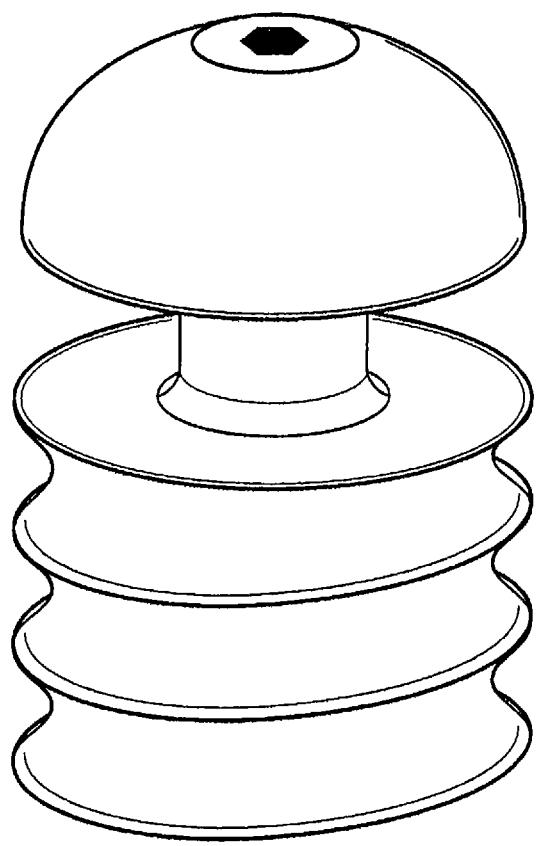
FIG. 7B is a lateral cut away view of an alternative embodiment of the coupling mechanism between the trailing end of the screw and the lofted chamber.
Figure 7C:
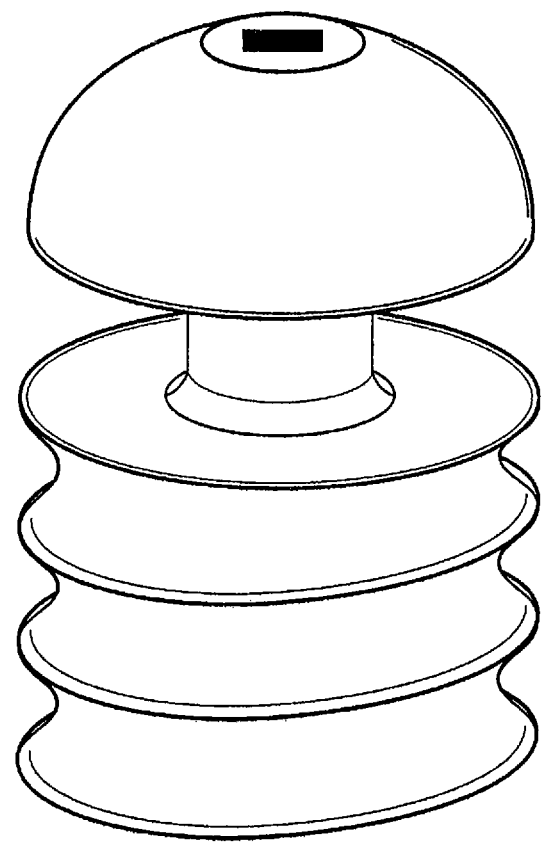
FIG. 7C is a lateral cut away view of another alternative embodiment of the coupling mechanism between the trailing end of the screw and the lofted chamber.

The trailing end achieves multiple purposes, including implantation of the device and locking the screws to the diagonal connectors. Firstly, as shown ion FIGS. 6A, the trailing end 6 is encased entirely within a purpose-specific central chamber 7 found in the leading end 8 of the diagonal connector 2. It is critical to note that this chamber 7 is of sufficient size such that the trailing end 6 will rotate freely and completely unencumbered therein during the insertion but prior to completely seating the screw into the target pedicle. Upon completely seating the screw into the pedicle, the leading end of the lofted chamber abuts the bone at the entry point of the pedicle, ultimately precipitating deployment of a pedicle screw locking mechanism. Specifically, the leading end of the lofted chamber forms an articulating shelf 10, which completely engulfs and surrounds the isthmus extending from the shaft of the screw to the base of the cylindrical head. This shelf provides an expanded surface area which maximally interfaces with the base of the cylindrical head. Augmenting this interface, the base of the cylindrical head and the apposing surface of the articulating shelf 10 of the lofted chamber are provided with corrugations/crenellations which, acting in concert and interfacing with each other, create a ratcheting mechanism. This mechanism, when deployed, secures and locks the screw in position. This is deployed by the advance of the screw into the pedicle, whereby the articulating shelf of the lofted chamber is brought against the bone surrounding the entry point to the pedicle. Once this has been achieved, the screw may advance to a very limited degree further, but the lofted chamber remains stationary against the bone. At that point, with a minimal additional advance of the screw into the bone, the apposing corrugations/crenellations will interface and then lock. Once the pedicle screw and the lofted chamber are locked, each diagonal connector acts as the trailing end of the respective pedicle screw. In this configuration, the leading end of the pedicle screw thereby becomes the input arm of the lever and the trailing end of the diagonal connector becomes the output arm.

The posterior or dorsal aspect of the lofted chamber is provided with an aperture through which the leading end of an insertion device may pass, thus gaining access to the insertion surface of the cylindrical head. Insertion can be achieved with the use of a hex-head, screwdriver, Philips head, or any other such insertion device. In this application, a device is disclosed which provides dual insertion shafts that rotate simultaneously, thus compelling both screws in the construct to be simultaneously rotated and inserted jointly into the pedicles. Alternatively, two screwdrivers may be used simultaneously. Regardless, it can now be fully appreciated that the configuration provided in which the cylindrical head rotates within the lofted chamber allows for insertion of the entire device in a unitized fashion.

The next portion of the diagonal connector, hereinafter known as the body of the diagonal connector, arises from the trailing end of the lofted chamber; it pursues a somewhat diagonal course, being directed posteriorly as well as towards the mid-portion of the target motion segment. This configuration is designed such that ultimately, the main body of each diagonal connector couples with the chamber housing unit, which is positioned between the screws of a target motion segment. It is the unique configuration of the diagonal connector which allows the chamber housing unit to be positioned in between the screws and thereby accomplish another important object of the invention, namely, to avoid intrusion upon the uninvolved facet complexes.

The coupling of the diagonal connector with the chamber housing unit is also accomplished through a unique configuration. In this coupling, there is a spherical enlargement of the main body of the diagonal connector at the point the diagonal connector passes through the wall of the chamber housing unit. This spherical enlargement is encased within a ball-bearing type socket which is incorporated within and monolithic with the wall of the chamber housing unit. The interface between the spherical enlargement of the diagonal connector and this socket therefore dictates the range of motion of the diagonal connector (and hence the diagonal connector-screw complex). For this reason, the spherical configuration provides the most complete range of motion, recapitulating the natural range of movement of the vertebrae and hence the motion segment; this is critical to the function of the invention as a whole. This coupling also provides the fulcrum for the first-class lever mechanism of the invention.

The trailing ends of the diagonal connectors are, furthermore, configured so as to serve as the interface with the fluid medium that is instilled into the chamber housing unit. This fluid medium shall hereinafter be known as the constraining medium. In the preferred embodiment, this trailing end is also represented by a spherical enlargement, known hereinafter as the dampening sphere. Utilizing a spherical configuration at this point again recapitulates the spherical range of movement that is demanded of the typical vertebral motion segment. It is worth clarification that the spherical enlargement of the body of the diagonal connector is separate and apart from the dampening sphere, which serves as the interface with the constraining medium.

It is this interface that creates the "fluid-lever" mechanism which represents the output arm of the lever. This ultimately provides the adjustable constrained motion to the target motion segment through the theoretical mechanisms of levers and fluid dynamics as reviewed above.

The dampening sphere is found at the trailing end and is monolithic with a short stalk which in turn arises from the spherical enlargement that couples with the wall of the chamber housing unit. This configuration again is important; this short stalk provides each dampening sphere in each chamber of the chamber housing unit to pass through approximately 90°; any pair, therefore, is provided with 180° of movement if the stalks taken together representing a semicircle. This again represents the maximal amount of movement that would be demanded from a motion segment.

Hence, as the result of this configuration, all movements of the vertebrae (normal range of movement as well as pathologically excessive) will be translated to the trailing ends/dampening spheres of the diagonal connectors; in that way, normal and excessive motion of a pair of target vertebrae (a target motion segment) interfaces with the constraining medium. Adjusting the output arm (fluid resistance) will then reduce excessive motion and modulates/re-establishes normal motion. This would (presumably) result from filling the chambers of the chamber housing unit with an exact amount of constraining medium to achieve the ideal degree of dampening/constraint of movement that will reduce pathologically excessive movement, and restore the movement of the motion segment to within an acceptable physiologic range.

Furthermore, owing to the geometry of the preferred embodiments in combination with the physics of a moment arm resulting in movement around a fulcrum, a minimal restriction/constraining of the output arm may result in a very substantial restriction of the leading end of the screws.

The chamber housing unit is envisioned to be, in general, substantially ovoid in configuration. It couples with, and is positioned between the diagonal connectors from each side of the construct (one chamber housing unit is present for each target motion segment in the construct) and specifically positioned so as to not intrude on the associated facet complexes or other osseous structures. Most specifically, the device is designed so as not to intrude on the superior articular process of the cranial facet complex in the construct, as well as not to intrude on the inferior articular process of the caudal facet complex. This substantially ovoid shaped structure contains within it a pair of chambers within which the trailing ends/dampening spheres of the associated diagonal connectors are found.

Both of these chambers, however, are contained within the chassis of a single chamber housing unit. The chamber housing unit is ultimately responsible for the primary object of the invention, which is the modulation of movement and, moreover, the reduction/elimination of pathologically excessive movement of a target motion segment. This is achieved through the independent interface between the trailing ends of the diagonal connector/screw complexes and the constraining medium contained within the two chambers of the chassis of the chamber housing unit, in combination with the chassis which acts as a stabilizing force, hence further equilibrating movement between the two trailing ends of the lever arms segment.

Each chamber may or may not be lined with an inner liner composed of a material such as polyester, latex, or other flexible material acceptable to the art. In this embodiment the constraining medium is instilled within the liner found on the inside of the chambers of the chamber housing unit. The chamber housing unit is provided with ports, hereinafter known as filling ports, through which the chambers can be accessed and the constraining medium instilled. These ports are provided with an access mechanism by which the medium is instilled and contained after instillation. This would be achieved via a perforatable diaphragm composed of latex, polyester, polyvinyl or any other substance known or acceptable to the art. Obviously a valve mechanism could also serve in this capacity.

Predicting how much constraining medium is necessary to accomplish the goals set forth is a critical challenge to the success of the operation of this device. This may be accomplished by either an empirical estimation by the surgeon or by a theoretical calculation.

In this method, a device is provided that consists of two shaft-like extensions arising from a central body. This device shall hereinafter be known as the flexion/extension gauge. At the leading end of each of these extensions, there is a cradle which reversibly couples with the outside of the lofted chamber found at the leading end of the diagonal connector. The cradle is coupled to the lofted chamber after insertion of the constrained motion device into the target motion segment, but prior to instilling any constraining medium into the chambers of the chamber housing unit.

Once the shaft-like extensions are coupled to the lofted chamber, the surgeon will spread these shafts apart, as well as compress them together. These movements will mimic or recapitulate flexion and extension movements of the spine. Sensors, either fiber-optic, spring-loaded, or mechanical, which are located in the central body of the flexion/extension gauge, will then provide a readout (presumably digital) from which the amount of constraining fluid/filling pressure of constraining fluid can be extrapolated. This is then accomplished, and the constrained motion device is now completed in terms of implantation.

In the setting whereupon two or more target motion segments require treatment, an additional embodiment of the diagonal connector must be disclosed. In this embodiment, the diagonal connectors at the cranial and caudal aspects of the construct are as disclosed and provided above. However, the connector which is located at the mid-section of the construct is unique insofar that rather than a single body arising from the trailing end of the lofted chamber, a "V-shaped" configuration arises from a central lofted chamber. Whereas the diagonal connector disclosed above is provided with a lofted chamber, a body, and a terminal portion, this "V-shaped," connector, hereinafter known as the dual action connector, again has a single lofted chamber; however, in this case, two extensions or "bodies," are provided: a cranial body of the dual action connector is directed posteriorly and cranially, coupling with the chamber housing unit which is cranial to the central connector. There is also a caudal body which is directed posteriorly and caudally, and couples with the chamber housing unit which is caudal to the central connector. The cranial and caudal bodies are both provided with a spherical enlargement which is seated within a socket comprising a component of the wall of the associated chamber housing unit. Additionally, recapitulating the structure of the diagonal connector disclosed above, both the cranial and caudal bodies have a terminal spherical component known as a dampening sphere which function as the interface with the fluid within the chamber housing unit and again serve as the mechanism for the reduction of excessive fluid. In this lofted chamber, there is still an aperture leading to a shaft that provides the surgeon with access to insert the screwdriver device that is being utilized. In this instance, the aperture is located on the trailing aspect of the junction of the cranial and caudal bodies.

There are yet several other, special circumstances. In the first of these special instances, disclosed herein is a variation by which a non-mobile construct is implanted; furthermore, in combination with the preferred embodiment that has already been disclosed, a construct is possible by which a non-mobile construct may be implanted at one level, while an adjustable constrained motion construct may be implanted at an adjacent level.

The preferred embodiment of a non-mobile embodiment of this invention would offer the same advantages that the mobile embodiment offers. Specifically, it would allow for ease in implantation insofar that it can be implanted in a unitized, completely assembled fashion. Secondly, the design of the trailing ends of the screws and the stabilizing chamber housing unit would prevent any intrusion upon the un-involved articular processes.

In this embodiment, there are again provided a pair of screws which are secured to the superior and inferior pedicles of the target motion segment. The trailing ends of these screws are then coupled with the diagonal connectors in the same fashion as the diagonal connectors found in the adjustable embodiment. However, in this variation, the central portion of the device is merely a solid component spanning from the trailing end of one diagonal connector to the trailing end of the other diagonal connector. This component shall hereinafter be known as central stabilizing unit, in contradistinction to the chamber housing unit utilized in the constrained motion construct.

It is well-known that there may be significant variations of the angles of the pedicles from level to level, particularly in the lower lumbar spine. The preferred embodiment disclosed above can easily adjust for such variations because of the spherical enlargement of the diagonal connectors, which allows the surgeon to change the angle of the approach to the pedicle. As there is no component in this alternative embodiment, another mechanism must be in place in this embodiment to account for this variation. This would ideally be solved by providing a trailing end to the screw which is substantially spherical, as would the chamber within which it is housed. This would allow for adjustment of the entry angle of the screw over a substantial range so that the screws could be placed using the optimal trajectory. One recognizes, accordingly, that the aperture in the lofted chamber encasing the trailing end of the screw is enlarged to account for the adjustments in the trajectory of the screw. Again, a ratcheting mechanism, or a mechanism by which the surface of the sphere is highly irregular, is provided to serve as a locking mechanism.

In the setting whereupon the surgeon merely wishes to implant a single-level non-mobile (fusion) construct, implantation of the central stabilizing unit will be primarily the same as the insertion of a single level motion-preservation embodiment described above will suffice.

A setting whereupon a combined construct is necessary can be contemplated. In such a setting, a central stabilizing unit is implanted into one motion segment while a spinal implant device is implanted into the adjacent level. The two constructs are joined by a dual action connector. It is safe to assume that any combination of stabilizing and motion preservation constructs can be implanted. This method for providing a restriction of excessive movement of the spine is particularly unique, useful, novel and non-obvious.

As implied in the "History of related art," section above, there is yet one additional consideration which may be preferred in certain circumstances. The value of restoring disc height when the degenerative process has led to a decrease in disc height remains controversial. Some surgeons believe that this is an exercise in futility, is neither needed nor desired and may result in disordered spinal dynamics at adjacent levels. Other papers, however, teach that restoration increase the size of the foramen leading to decompression of the exiting nerve roots, as well as other advantages. There is also some very preliminary data to suggest that the restoration of height might actually have a salutary effect on the degenerative process affecting the disc. The answers are still forthcoming.

It is, therefore, an important object to provide an embodiment that can impart an element of distraction of the disc space between the vertebrae comprising the motion segment. This is true for the constrained/adjustable movement constructs, as well as the non-mobile/fusion constructs. Achieving such a construct for the constrained/adjustable movement construct will be considered initially.

This can be accomplished by providing a variation of the embodiment of the chamber housing unit in which this chamber housing unit can be expanded in the craniocaudal dimension. Therefore, rather than the chamber housing unit being a single, monolithic structure with two chambers, in this embodiment, it is represented by two individual components which are slidably coupled to each other at their junction. Bach of these are in turn are provided with a chamber to house the dampening sphere of the respective diagonal connector to which they are coupled.

However, these two units, which shall be referred to as the expandable chamber sub-units, each have a have a flattened end at their junction, which in the fully collapsed embodiment, abut each other. In order to achieve the specific object of this embodiment, the cross-section of one of these units is slightly larger than that of the second unit. The first unit is also provided with extensions from the end which envelope the second unit for an undefined length. It can be appreciated that such an arrangement will create a potential space between the ends of the first and second units. The potential space, known hereinafter as the restoration space, can hence be expanded to be equal to approximately the length of the extensions. Of course, the inner surface of the extensions and the outer surface of the second sub—unit are provided with notches, ledges, or protrusions so as to prevent the two units from becoming over-distracted and dislodged from each other, and hence maintain the structure of the unit.

A mechanism is provided for instilling a fluid medium into the restoration space between the trailing ends of the sub-units. This may be achieved either by providing perforatable diaphragms in both trailing ends through which a needle may be passed and the medium instilled. Alternatively, there may be a channel within one or both sub-units, this channel extending from a perforatable diaphragm to the potential space. By instilling fluid medium into this channel (and hence into the potential space between the trailing ends of both sub-units, distraction of the chamber housing unit—and ultimately the target motion segment—can be achieved and maintained. After satisfactory positioning and securing the pedicle screws, a simple distraction device such as is commonly used in many systems and widely available is introduced into the operative field. The device is used to distract the vertebrae and restore disc height. Once this is accomplished, the space which has been created between the trailingmost ends is filled by some non-compressible or nearly non-compressible fluid medium such as densely-packed microspheres. The distraction is thus maintained. Obviously, an alternative mechanism would be instilling the fluid medium into the restoration space, and using the force of the fluid expanding the chamber to distract the disc space.

In yet a further alternative embodiment, rather than using a fluid medium in the restoration space to maintain the distraction of the device, a simple ratcheting mechanism or any other mechanical system for maintaining the distraction can also be envisioned an is included within the spirit of the application.

An alternative embodiment is to provide an expandable chamber between the two sub-units, the expandable chamber being provided with expandable walls so that as the chamber expands, these walls will re-configure themselves accordingly.

In the setting of a non-mobile construct capable of establishing and maintaining distraction, as opposed to the rod construct disclosed above, each diagonal connector is continuous with a hemiovoid shaped component, known from this point forward as an expandable stabilizer. The expandable stabilizer has a rounded leading end which is continuous with the diagonal connector, and a flattened trailing end which abuts the flattened trailing end of the other hemi-ovoid structure in the construct. In the complete embodiment of this arrangement, there is a first expandable stabilizer and a second expandable stabilizer, with the first one being slightly larger in diameter/cross section than the second. In being configured thusly, the first expandable stabilizer is provided with extensions which pass over and closely approximate the trailing end of the second expandable stabilizer. The interface between the extensions of the first expandable stabilizer and the outer surface of the trailing end of the second is provided with a ratcheting mechanism, such that if these two components are distracted, the ratcheting mechanism will maintain that distraction in the desired position.

Those familiar with the art will readily recognize that a number of modifications and alternative embodiments are obvious. A number of such embodiments are discussed below, and other may be conceivable. All such embodiments are and remain within the spirit and scope of the invention.

Surgical Technique for a Preferred Embodiment

When using a minimally invasive approach to implanting the device, a purpose—specific set of instruments can be used to best accomplish this implantation. The entry point/skin incision would be identified with the use of a template which allows the identification of entry points in the skin, which would give the best access to subcutaneous structures. Once the ideal entry point to the target pedicles has been identified, skin incisions are accomplished. The next instrument should hereinafter be known as a pedicle trocar, consists of two parts that are reversibly coupled. There is an outer sheath, which consists of a leading end, a shaft, and a trailing end. The leading end of the outer sheath is generally cone shaped, with varying degrees of fullness of its sides. There is aperture at the apex of the cone shape, this aperture in turn, is continuous with a channel extending the length of the apparatus. That aperture accommodates a second, central component to this device. The walls of the leading end may be smooth, or may have mild corrugations to them; these corrugations are consistent with enabling a twisting motion of the device as it is passed from the entry point in the skin to the base of the pedicle. The shaft of the outer sheath is a round, cylindrical structure, which can be used as a stabilizing handle while passing the device, and which allows the second central component of the device to pass through. The shaft is presumably of varying lengths, in conjunction with the size of the patient and other surgeon desires and requirements. A critical aspect of the outer sheath is that it is composed entirely of plastic, polyethylene, or some other radiolucent substance. The importance of this is underscored when the second component of the device is revealed, and the complete use of the device is disclosed. The trailing end of the outer sheath is provided with a pair of brackets, in the preferred embodiment, which accommodate the third component of this device, that component being known as the handle locking shelf.

The second component of the pedicle trocar is an inner shaft which passes through the outer sheath. This is also provided with a leading end, a shaft, and a trailing end. The leading end of the central shaft, in the ideal, preferred embodiment, is the only component of this device that is composed of a radiopaque metal substance. This leading end is provided with a sharpened tip, and thencefrom, for a short, undefined interval, the sharpened tip is continuous with a threaded shaft. The remainder of the shaft of this component is a solid, non-threaded shaft, which is designed to pass through a channel which has been provided within the outer sheath, and fashioned in such a way that the outer diameter of the shaft is just slightly smaller than the inner diameter of the channel to which it passes, so that it may fit snuggly, and not be hindered while rotating. The trailing end of the inner shaft is designed to conform to any number of handle like embodiments, either a T-handle, a rounded handle, or an elongated handle. In the preferred embodiment, a rounded handle would be considered ideal. The dimensions of the inner shaft are such that when the inner shaft is passed through the outer sheath, and be initially position such that merely the sharpened leading end of the inner shaft would protrude through the aperture at the leading end of the outer sheath. The inner shaft is initially position in this fashion for the use of the positioning of the locking shelf. The locking shelf, which is the third component of the pedicle trocar device, is utilized at the trailing end of the device, and is designed so that it has a flattened central piece, which is generally configured so as to substantially cover the trailing end of the outer sheath. At the lateral most edges of the flattened central piece, there are two orthogonal extensions, which are provided with tabs such that they can lock into the brackets which have been provided to the trailing end of the outer sheath. In the center of the flattened horizontal piece, there is a cutaway, which permits this locking shelf to be passed around grooves that are provided into the trailing end of the shaft of the inner shaft of the pedicle trocar. This allows the pedicle trocar to be locked in an initial position by which merely the leading most end of its tip is seen protruding through the aperture at the leading end of the outer sheath. When in this deployable position, the locking shelf is reversibly coupled with the trailing end of the outer sheath, and in that fashion, that is to say when it is locked against the brackets provided on the trailing end of the sheath, then the flattened horizontal area passes around the trailing end of the inner shaft, thus locking it and preventing it from displacement during the initial passage of the device into the back of the patient. When the device is in a position such that the leading end of the inner shaft is in good position for entry into the pedicle, the locking shelf is removed and the inner shaft is then passed into the base of the pedicle. This is done while maintaining the outer sheath in place. Because only the leading end of the inner shaft is radiopaque, understanding its position on x-ray is readily accomplished. Obviously, such a maneuver would have to be performed under fluoroscopic guidance, although some surgeons might even choose to perform such a maneuver under CT guidance in facilities where such technology is available.

Hence, once the incisions have been made to accommodate the placement of the pedicle trocars, the trocars are introduced into the surgical field. The leading ends of the trocars are passed through the incisions and with a rotating movement are advanced through the soft tissues to the base of the pedicle. Again, given the fact that there is not a great deal of metallic artifact present, interpretation of the position of the leading end of these trocars with respect to the pedicles is readily accomplished. Once the leading ends of the trocars are passed through, the surgeon may choose to pass this through a variable depth and remove it. Once the surgeon brings the inner shaft down the point where the leading end of the inner shaft has made contact with the base of the pedicle, then the locking shelves are removed. The leading ends of the leading shafts are then passed into the base of the pedicles, to varying depths. The outer sheaths, of course, are still in position.

At that point, the incision is enlarged so as to essentially connect the two vertical incisions. The retractor is then introduced. The retractor is a tube-like structure, which is provided with a unique expandable element. Another unique feature of the retractor is that at the caudal and cranial ends of the retractor, the retractor has been configured so as to recapitulate the cylindrical shape and size of the outer sheath, and can be slid over the outer sheaths and directly down to the base of the pedicles as well. The retractor can then be secured in position with a number of different maneuvers.

In the preferred embodiment, the retractor is secured into position with a C clamp that is connected to the operating table, and which is provided with a leading end to its arm that can be, in a sterile fashion, secured to the retractor in some fashion. This then holds the retractor in place, the retractor of course having been passed around the outer sheaths of the pedicle trocars.

Upon doing so, the inner shaft is removed entirely from its position within the outer sheath. At that point, a drill may be passed through the pedicle to the desired depth. The outer sheaths are then also removed, and with the retractor maintained in position, the retractor serves as a guide for passage of the device into final position. In a variation, the outer sheaths of the pedicle trocars may be uniquely designed such as to allow a portion of the wall of the outer sheath, which is reversibly coupled to the rest of the sheath, to be removed. When this is done, the sheath will assume a "C-shape" or "reverse C-shape" as viewed from the top. The unitized device can then be passed through these sheaths (which are further stabilized by the retractor), with the lumina of the sheaths guiding the screws and the openings in the side of the "C-shape" or "reverse C-shape," serving to accommodate the diagonal connectors. The chamber housing unit would be found between the two sheaths, of course. This is accommodated by the shape of the retractor. The body of the chamber housing unit is further stabilized by a separate device.

In the preferred embodiment, a separate apparatus stabilizes the chamber housing unit and serves to also stabilize a dual-tipped screwdriver is passed into the retractor and used to implant the device. This apparatus shall hereinafter be known as the insertion handle, as it serves not only to "insert" the assembled, unitized device, but also serves to deliver the pedicle screws into the target pedicles. This device shall be further disclosed and described below.

Then, the flexion/extension measuring device, which shall also be described further below, is applied and a readout is obtained to guide the surgeon in terms of filling the chambers with constraining medium. Once the medium is introduced, the operation is complete and the surgeon closes the incision.

Obviously, in most instances these would be implanted bilaterally. Presumably, this could be readily achieved by two surgical teams working simultaneously. Alternatively, a single surgeon would achieve the same results with an increased amount of operative time.

Post Surgical Adjustments of the Amount of Constrained Motion of the Device

One very significant aspect of this set of devices and methods is that unlike other systems currently being utilized, this system will permit post-operative adjustments of the amount of constrained motion the device imposes upon the target motion segment. This could be done at any point in the future with respect to the surgical date.

This can be done by inserting a purpose-specific needle into the access port (aperture) on the dorsal aspect of the chamber housing unit. Ideally, this can be done percutaneously or can be done through a minimally invasive incision. By adding additional fluid the system will make it more difficult for the lever arm to move through the fluid and hence, will render the target motion segment less compliant. Alternatively, by removing constraining medium from the system, a more compliant system will be created. It is anticipated that a separate application describing a kit to accomplish these adjustments will be forthcoming.

General Embodiments/Alternative Embodiments

There are, in general terms, two sets of embodiments of this device:

In the first case, the device is unitized and is implanted in its completely assembled, functional form, as provided above.

Conversely, in another set of embodiments, the device is assembled in situ, with some components being initially implanted, and the remaining components being coupled to those initially implanted.

The device has already been disclosed as it appears in its completely assembled configuration which is implanted in a unitized configuration, as well as an embodiment and method for implantation in which the device is assembled in situ. Individual components, along with alternative embodiments, will be disclosed in greater detail below. Subsequently, the unitized and non-unitized embodiments are to be discussed individually, reviewing the importance, advantages and disadvantages of each.

Multiple embodiments of the various components are disclosed, as well as examples of various combinations of these embodiments, these combinations designed to achieve the goals of the invention. It is recognized that while various, but not all possible, combinations are disclosed, all conceivable combinations are within the spirit and scope of the invention.

Additionally provided are a number of devices used to implant the invention in its proper position within the patient. Also disclosed is a method for intraoperative identification of the target motion segment, as well as a surgical technique for the implantation of the alternative embodiments of the invention.

Regardless of the embodiment or method of implantation (unitized vs. non-unitized), the device is composed of at least three elements: two threaded pedical screws 1, also known as bone fasteners, and a central, functional component, hereinafter known as the chamber housing unit.

Pedical Screws

The preferred embodiment of the threaded bone fastener, also referred to as a bone screw or pedicle screw, has been disclosed above. Alternative embodiments providing for a straight shaft such as a nail-like structure is also plausible, and is incorporated within the spirit and scope of this application. Additionally, a shaft with longitudinal rather than the classic perpendicular threading is also conceivable, as is a shaft with longitudinal spiral threading.

Another alternative embodiment involves an alternative embodiment of the pedicle trocar, and is also described above as an alternative surgical technique.

In this embodiment, the leading end of the pedicle trocar provided is a small pin or spike-like structure. It has an extremely sharp leading end, which readily facilitates passage into the base of the pedicle. The leading end of pedicle trocar insertion device will reversibly couple with the trailing end of this pedicle trocar, and the trocar is passed into the entry point of the target pedicle, allowing the trailing ends to remain outside the bone. When this has been accomplished, the insertion handle is removed and the position is again verified. This may be more readily accomplished given the small size of this pedicle trocar, discouraging radiographic artifacts and allowing extremely accurate radiographic identification.

In this embodiment, the leading ends of the bone fasteners are modified and fashioned in such a way as to couple with the trailing ends of the pins/spikes which are protruding posterior to the entry point of the target pedicle. Once this coupling is accomplished, the pins/spikes then become the leading ends of the bone fasteners. This technique would provide for very accurate placement of the pedicle screws. The device is then completely inserted into the target segment.

The threading of the shaft is of an adequate pitch, sharpness, and ratio of inside to outside diameter so is to provide optimal bone purchase. The shaft may be of varying lengths, so as to provide the surgeon with options relating to the specific anatomy of the target motion segments as they may vary from patient to patient. The geometry of the trailing ends of the bone fasteners is a unique and non-clear aspect of the invention that prevents intrusion upon the adjacent facet joints, which, as stated, is yet another object of the device.

The preferred embodiment having already been disclosed, multiple alternative embodiments of the trailing end of the bone fasteners are also conceivable; this is particularly true since it is modifications of this component that dictate whether the device is implanted in a unitized fashion or will require assembly in situ. Multiple alternative embodiments of the interaction between the trailing ends of the bone fasteners and the chambers within the chamber housing unit, as well as the chamber housing unit itself, are also provided.

The preferred embodiment of the coupling of the trailing end of the screw (cylindrical head) to the leading end of the diagonal connector (lofted chamber) is accomplished by the interface of a locking ratchet mechanism provided on both components. Multiple variations of the cylindrical head can be anticipated, and these can include a simple, flat disc arising from a stalk representing the connection from the trailing end of the shaft of the screw to the disc, as well as a sphere, as well as any other geometric structure that can be connected by the aforementioned stalk, and can rotate freely within the lofted chamber of the diagonal connector. The critical importance of the connecting stalk cannot be overstated; this translates rotation of the head (by the screwdriver device) to the shaft of the screw. Moreover, this stalk must be narrow enough to create a substantial surface area for the ratcheting mechanism to fully realize its required role.

Whether discussing the preferred or alternative embodiments, the trailing end of the bone fastener is unique insofar that it does not terminate in a typical screw head. The preferred embodiment has been already disclosed. In an alternative embodiment in which the invention is assembled in situ, the trailing end is no longer threaded. Furthermore, in such an embodiment, the diagonal connector is not a separate component but rather monolithic with the trailing end of the bone fastener.

It is designed, rather, in such a fashion so that as the shaft of the bone fastener emerges from the bone, the shaft of the trailing end is provided with an approximately 80-160° angle. This is leading then into a substantially diagonal portion of the trailing end which is substantially perpendicular with the long axes of the shaft of the bone fastener. Therefore, in some embodiments in which the device is assembled in situ, the bone fastener is monolithic with the diagonal connector, and the trailing end of this monolithic structure is found coupling/interfacing with the chamber housing unit.

The trailingmost end is then directed into the chamber housing unit at an angle from this diagonal portion. This can be virtually any angle, depending on the embodiment, but in the ideal circumstances, an angle of about 40° to 90° with respect to the diagonal portion would be the most favored configuration. However, it must be emphasized that any combination or sequence of angles may be acceptable and is within the spirit and scope of the invention. Furthermore, it is anticipated that data will be developed such that ultimately, the ideal angles for such a device in a particular patient population will be empirically determined. It is recognized that it may be conceivable that various subpopulations of patients, such as male vs. female, age related changes, and body habitus, may require different angles and configurations for this portion of the device.

The terminal portion of the trailing end of the bone fastener is then designed to irreversibly couple with the chamber housing unit of the invention. This relationship essentially holds true and is the same for all embodiments, whether the device is inserted as individual components and then assembled and constructed in situ, or embodiments in which the device is unitized and inserted fully assembled.

Whether the entire bone fastener is a monolithic structure or alternative embodiments are employed, the coupling mechanism itself can be any of a variety of embodiments. It can be represented, in its simplest form, as an enlargement of the terminalmost end of the bone fastener after the diagonal portion passes through an aperture in the wall of the central chamber housing unit. This enlargement is then seated and irreversibly coupled within the central portion of that unit. This coupling is in part due to the presence of a gasket made of flexible material such as latex or a compressible polyester/polyethylene, and surrounding the aperture. In such an embodiment, it is imagined that these terminal enlargements or swellings may be very slightly larger in diameter than the aperture through which it will pass. As a corollary, it would then be anticipated that there would also be provided an insertion instrument that would "pressure fit" the terminal enlargement or swelling through the gasket surrounding the aperture and accomplish this irreversible coupling. Other coupling mechanisms will also be provided.

In another coupling mechanism, the wall of the chamber housing unit is provided with a mobile sphere that is encased within a ball-bearing mechanism, similar to that found in the preferred embodiment/unitized device described above. Furthermore, within the chamber housing unit of this embodiment, there is an extension from this mobile sphere that is continuous with and terminates in a sphere acting as the dampening sphere of the preferred embodiment, again recapitulating that configuration. However, as this embodiment is constructed in situ, there must be a location for the attachment of the trailing end of the monolithic bone screw. It can be envisioned that ideally, that coupling occurs at the exterior surface of the mobile sphere, which is provided with an aperture leading to a channel/chamber into which the trailing end of the bone screw can be inserted and couple. This coupling can be accomplished with the use of pressure fit, ratcheting lock, threaded junction, or any other conceivable mechanism known or acceptable to the art. Upon insertion of the trailing end of the screw into this mobile sphere, the movements of the vertebrae are translated to the sphere, which then translates the movements (in the reciprocal fashion described above) to the dampening sphere within the chamber housing unit. The primary mechanism of the invention is then deployed.

Alternatively, there can be envisioned an extension from this sphere that can be coupled with the trailing end of the bone screw at any point along the course of the screw from the trailing end of the shaft to the mid-position of diagonal connector. Given the monolithic structure of the screw, coupling at any point along that course will have an equivalent result.

Alternative embodiments of the trailingmost end of the bone fasteners must be provided for embodiments in which the entire device is implanted fully assembled. These embodiments will be completely disclosed further on in this application, but even a cursory examination of the challenges that must be overcome in implanting a fully-assembled mechanism revels that in such a scenario, monolithic bone fasteners cannot be utilized. In such an instance, the diagonal portion of the bone fasteners is a separate component from the vertical shaft, with these two components provided with a mechanism by which the shaft can rotate independently from the diagonal portion. Preferred and alternative embodiments of these disclosures are completely described below.

Chamber Housing Unit

The chamber housing unit itself consists of a cylindrical shaped structure, which may be monolithic, or may be multi-component. It is anticipated that in the preferred embodiment, it is multi-component. The central, cylindrical shaped body of this element is provided with apertures on its inferior and/or terminal aspects. It does not have, per se, a leading or trailing end, but rather is positioned between and coupled to the trailing ends of the bone fasteners that have been secured into the pedicles of each of the vertebra involved in the construct.

This chamber, in turn, will contain any fluid or ballotable substance. It is imagined that in the ideal embodiment, this would represent a fairly viscous liquid or a fairly firm ballotable substance such as foam, sillicagel, microspheres and/or nanospheres.

The chamber housing unit is envisioned to be constructed of titanium, stainless steel, other alloys, or any substance known or acceptable to the art. The interior shall be lined, in a preferred embodiment, with a flexible but firm substance such as latex, polyethylene, or any other substance that can serve as an interface between the trailingmost end of the bone fastener and the interior of the chamber. A potential space is created between this liner and the interior wall of the chamber, and the constraining medium which modulates the movement of the trailingmost end of the bone fastener is ultimately instilled into this potential space.

In the preferred embodiment to be assembled in situ at a single motion segment, there is a threaded bone fastener to be inserted into the pedicle of the superior and inferior vertebrae of the motion segment. The trailing ends of these are then coupled with the chamber housing unit. The trailing ends of these bone fasteners are different and unique contingent upon whether the embodiment is to be assembled in situ or if the embodiment is to be inserted as a completely assembled, unitized construct.

If the embodiment is to be assembled in situ, each screw is passed separately into the target pedicles, followed by coupling of the chamber housing unit to the trailing ends of the bone fasteners. In such an embodiment, the trailing ends of the bone fasteners are provided with a unique feature in which, rather than ending in a configuration that would typify the trailing end of a screw (some variant of a screw head), the trailing end is continuous and monolithic with a diagonal portion that extends from the trailing end of the shaft of the screw and, when ultimately inserted into its proper position, is directed towards the trailing end of the other bone fastener in the construct. This diagonal portion may also be directed somewhat posteriorly, as viewed in the sagittal plane, and terminates in bulbous enlargement. This bulbous enlargement is that portion of the trailing end which is coupled with the chamber housing unit. The trailing end of each screw is coupled with a separate chamber within the chamber housing unit. The chamber housing unit can be enlarged in the craniocaudal dimension, so that distraction can be applied and maintained at the target motion segment. The chamber housing unit can then be filled with a medium which will create the degree of motion restriction/constrainment desired.

In an embodiment in which the device is inserted in a unitized fashion, the trailing end of the bone fasteners described above is divided into two coupled portions. The trailing end of the bone fastener proper terminates in a spherical or a variant of a spherical configuration. On the trailingmost or dorsal aspect of this sphere is found a feature that will accommodate an insertion device such as a hex-shaped, Philips-head, or standard screwdriver.

The diagonal portion (hereinafter known as the diagonal connector) disclosed above is a separate component which is coupled with the spherical terminal portion of the bone fastener. This coupling is accomplished by the leading end of the diagonal connector, which is a cup or "loft" shaped configuration, the long axis of which is continuous with the long axis of the shaft of the bone fastener. This portion of the diagonal connector shall hereinafter be known as the lofted chamber. The diagonal portion of the diagonal connector is then directed at a 45-90° angle from its junction with the lofted chamber.

The lofted chamber is fitted around the spherical terminal portion of the bone fastener. There is an aperture on the dorsal aspect of the lofted chamber, at its junction with the remainder of the diagonal connector. This aperture provides the access necessary for the screwdriver/insertion device to be inserted into the spherical terminal portion of the bone fastener, thus allowing the device to be inserted into the target pedicles. The spherical trailing end of the screw is almost completely encased within the lofted chamber, except for an aperture found at the leading most end of the lofted chamber. This aperture allows for a stem-like extension from the trailing end of the shaft of the shaft of the screw to the base of the sphere. This extension is approximately half of the diameter of the sphere. The leading most end of the lofted chamber is provided with shelf-like extensions that create the aperture through which this extension passes, these extensions passing under the base of the sphere and creating an aperture just slightly larger than the extension which it accommodates. The interior of the lofted chamber is then hollowed-out so as to closely contour the exact shape of the spherical trailing end of the screw.

A critical issue challenging any motion preservation device is the excessive strain placed on the purchase of the screws by the ongoing motion of the entire construct. Therefore, any feature that would increase the security of the purchase of the screws would offer additional advantages.

Herein several options for achieving this endpoint are disclosed. In the preferred embodiment, a unique and novel arrangement between the configuration of the base of the sphere at the trailing end of the screw, and the base of the lofted chamber. In this arrangement, the sphere is not completely round; rather, the base, which is in close approximation to the leading most end of the lofted chamber, represents a flattened disc.

The trailing end of the diagonal connector then terminates in a similar bulbous enlargement which is, in turn, coupled with the chamber housing unit. Again distraction and instillation of the constraining medium are accomplished in the same manner that these maneuvers are accomplished in an embodiment in which the device is assembled in situ.

There is an alternative embodiment of the horizontal and terminal portion of the bone fastener which may also be a preferred embodiment from a manufacturing perspective. In this alternative embodiment, the trailing and terminal ends of the bone fastener are represented by an arching configuration, rather than the series of angles described above. In this arching configuration, the critical issue is that the geometric relationship between the terminal portion of the bone fastener and the long axis of the shaft is maintained and is constant. As shall be shown later, this geometry creates a "pivot point" as the trailing end of the bone fastener enters into the chamber housing unit. This is a central and critical aspect of the invention. The importance of this "pivot point" becomes apparent if the relationship between the movement of the long axis of the shaft and the movements of the terminal portion within the chamber housing unit are examined.

As the target motion segment moves in accordance with the movement of the spine through the physiologic range of movement, the movement of the vertebrae comprising the target motion segment is translated through the pellicles to the shafts of the screws. The individual "pivot points," in turn, permit the shafts to translate the movement to the terminal ends of the screws, which are located within the chambers of the chamber housing unit. It is at this point that the mechanism within the housing chamber units provides resistance to the movement of the terminal portion of the screw. This resistance is then translated back to the shaft of the screw, and ultimately, through the relationship of the shaft to the pedicle, back to the vertebrae comprising the motion segment. In the example of excessive physiologic movement as the result of incompetent disc/facet joints secondary to degenerative disease, the resistance provided by the chamber housing unit and translated back to the vertebrae will damp down or limit this excessive movement.

In the preferred embodiment, the terminal portion of the trailing end is anticipated to have an enlargement, such as a bulbous enlargement, which in the assembled device is housed within the chamber housing unit. This enlargement is expected to be present regardless of whether the device is unitized and inserted fully assembled, or if the device is implanted and assembled in situ.

It is expected that in the setting in which the device is assembled during implantation, this enlargement may be useful for insertion into the chamber housing unit. As such, it would be expected that this enlargement would be passed through an aperture on the inferior or inferolateral aspect of the housing chamber unit. This aperture is fitted with a gasket or flexible ring, creating an aperture that is slightly smaller in diameter than the largest diameter of the bulbous enlargement. As the enlargement is passed through, the gasket or flexible ring can be momentarily distorted, allowing the passage of the enlargement in a mechanism similar to a "pressure-fit." This therefore creates a relatively irreversible coupling of the two elements. Of course, any other coupling mechanism can also be utilized to engage the terminal portion of the trailing end with the chamber housing unit.

Another critical component of the device is the junction of the diagonal connector and the wall of the chamber housing unit, specifically the point at which the diagonal connector passes through the wall prior to its termination within the chamber. There are at least three different configurations of this junction which would allow for this junction to provide motion to the device. These include a spherical connector that allows freedom of moment around 360 degrees, a partial sphere which provides a limited range of movement less than 360 degrees, and a single plane hinge.

In another object of this invention, it is anticipated that in the ideal embodiment, the surgeon would be able to adjust the amount of dynamic mobility/flexibility/resistance of this system by adjusting the amount of medium that is placed within the chambers. This is achieved by recalling that flexibility in the system arises from the interface of the terminal end of the bone fastener within the chamber, or within the sphere that is then positioned within the chamber. Hence, if there were a patient in whom it was felt that only a slight amount of mobility would be necessary at a specific level, then these chambers could be more density packed, thus limiting the motion of the terminal ends of the bone fasteners within the chambers (And hence the flexibility of the system at that level). On the other hand, consider a scenario in which a greater flexibility would be desired; in this instance, more loosely packing the chambers would permit a greater amount of flexibility. It is conceivable that as more information is developed, and as data and experience are gained, it may become apparent that different anatomic levels (i.e. L4-5 vs. L5-81) may require different amounts of pressure/resistance/mobility to function optimally.

The chamber housing unit of the device has been previously referred to and is here and now disclosed more completely. The chamber housing unit of this device provides the mechanism which ultimately allows this invention to govern the movement of the target motion segment in the variety of planes that comprise the normal range of movement of that target motion segment. The movement is principally governed as the result of the interface, and specifically the resistance between the trailingmost end of the bone fasteners and the ballottable fluid within the chambers of the chamber housing unit of the device. In the ideal, preferred embodiment, a mechanism is herein provided that permits the trailingmost ends of the bone fasteners to engage in movements that would ultimately provide flexion to the motion segment as well as providing extension, lateral rotation, lateral bending and a very limited amount of physiologic translation if desired. This is accomplished by providing a trailingmost end of the bone fastener with a spherical enlargement. That sphere, in turn, is seated within a chamber in the chamber housing unit of the invention. Embodiments of the walls of the chambers include a chamber that is represented by a single fluid-containing compartment as well as a chamber that is occupied by multiple fluid containing compartments. Again, it is expected that the surgeon can fill the fluid containing compartment with any ideal medium, and that he/she can also fill the compartment to varying degrees thus providing more rigidity or more flexibility to the system. One can also envision that the viscosity of the medium that is used could affect the flexibility or rigidity of the system and this creates yet another opportunity for making this system a variably controlled system.

In an embodiment in which the chamber is occupied by a single, fluid-containing compartment, there is an expandable, flexible membrane that is secured to the gasket, but not to the inner walls of the chamber. This arrangement will create a potential space between the inner walls of the chamber and flexible membrane. This membrane is composed of latex, flexible plastic, polyethylene, or any flexible substance known or acceptable to the art. As the membrane is secured to the gasket, it will surround the spherical terminal portion of the trailing end of the bone fastener which is seated within the chamber. Once the fluid medium has been placed within the potential space between the membrane and the inner walls of the chamber, the ability of the terminal end to move within the chamber is affected by the presence of the fluid within the chamber. As has been previously stated, a densely-packed, viscous fluid will have a greater limiting factor on the terminal end (and hence the motion segment) than a less-viscous fluid. Hence, it can even be postulated that perhaps different media may be utilized in specific scenarios. A port is provided which permits the placement of the medium within the potential space.

In a similar fashion, an embodiment in which multiple fluid-containing compartments are created by the use of multiple ballottable membranes. In this setting, these multiple membranes are secured or tethered to various points of attachment along the inner walls of the chamber, such as the corners, thus creating a construct which again provides resistance to the free movement of the terminal portion of the bone fastener. It must be recognized that in order to fill all of these compartments, they must all be in communication with one another, or multiple ports must be provided to the chamber. An advantage of the latter scheme is that the surgeon would have the option of differentially filling one aspect of a particular chamber more than another, which may be desirable in certain, specific clinical situations.

In an alternative embodiment, rather than using a series of ballotable chambers filled with a fluid medium, one can envision that the trailingmost end of the bone fastener may be encased within a chamber in which rather than fluid medium, resistance is provided by mechanical means, such as springs.

In one alternative embodiment, the trailingmost end of the bone fastener is encased within the chamber, as previously described. The chamber is provided with a series of multiple flat or slightly curved plates which then slidably interface with a spherical or a polygonal; multi-faceted trailing end of the bone fastener. On the other side of these plates there, is found a number of mechanisms that provide resistance and thus govern the amount of constrained motion that is being applied to the system. This is accomplished by a series of springs or resistance coils which are continuous with or connected to the flattened plates on one side, and on the other side are connected to the inner wall of the chamber. In such a construct, the spring or resistance coil is (obviously) connected to the plate on the opposite side of the side of the plate that interfaces with the trailingmost end of the bone fastener. These springs/resistance coils then provide resistance to the trailingmost end of the bone fastener when movements of the motion segment compel the trailingmost end of the bone fastener to move in various directions within the chamber of the chamber housing unit of the invention. This resistance therefore provides the mechanism for the constrained stabilization. This resistance accomplishes the goal of the invention, which is to prevent excessive movement of the motion segment while avoiding the establishment of rigid stabilization.

In another, alternative embodiment, there is again a series of plates that interface, but are not coupled to, a polygonal multifaceted trailingmost end of the bone fastener. In this embodiment, this series of plates is again coupled to a mechanism that provides resistance, that mechanism being coupled to the side of the plate which is opposite to the side of the plate that interfaces with the trailingmost end of the bone fastener. In this instance, the mechanism that provides resistance is in the form of one or more piston type mechanisms, similar to a shock absorber. It is envisioned that for each of several directions, there is at least one small piston, encased within a cylinder, which is directly connected to the plate. A variety of media can then be provided within the small cylinder to provide resistance to the cylinder. Resistance to the translation of this piston in the cylinder could be provided by a ballotable medium, such as those media disclosed above with which the chambers are filled.

In one embodiment of such a mechanism of resistance, the plate is interfacing again with the ballotable chamber. This is similar to the mechanism that is proposed in the preferred embodiment above. This ballotable chamber permits some movement of the plate, but constrains the trailingmost end of the bone screw from excessive movement. In this embodiment, it can be imagined that these ballotable compartments can be filled at the time of implantation, and thus the surgeon can, once again, make a judgment about the amount of resistance he wants to impart upon the system, and hence the amount of constraint of movement that the stabilizing system provides.

In yet another embodiment, there is a piston type mechanism which can represent a piston of any size and geometric shape within a cylinder fashioned to accommodate the piston. The piston is coupled or continuous with the slidable plate, and within the chamber is either a viscous fluid or a coil which is resistive to movement. In this mechanism, it can be imagined that there may be various surgical options of the center portion of the device, with those surgical options being contingent upon the degree of resistance within the coils. This can range from coils that offer a little resistance, to coils that are so resistant to movement that they impart significant governing affect upon the stabilization provided by the system. This again allows the surgeon to make a choice in how much resistance is imparted into the system overall, and hence, how much movement the system will allow the target motion segment to undergo.

In another embodiment, the plates are again interfacing the slidable fashion with the trailingmost end of the bone fastener, and on the other side of this interface is a series of rocker arms or levers which also interface with the plates. These rocker arms or levers are provided with a ratchet type mechanism on one end, with the other end interfacing with or even coupled to, the plate. The rocker arms are secured to a bracket and with the ratcheting mechanism in place, can rotate around the central axis of the bracket, which serves as the moment of rotation. As the multifaceted trailing end of the bone screw interfaces with the slidable plates, that movement is in turn translated to these rocker arms, which will allow the plates to move with some resistance as the result of the ratcheting mechanism. This is not an ideal embodiment, although it is included principally because it is within the spirit and scope of the invention.

In yet even another alternative embodiment, movement resistant coils are continuous with the walls of the chamber at one end of the coil, and the slidable plate on the other end of the coil. In such an embodiment, the coil is designed to be pushing out, rather than contracting like a spring, such that when movements of the head of the screw compel the plate against the coil and cause the coil to be somewhat compressed, the coil provides resistance (which is a critical component of this invention) and can return to its primary position when the motion segment returns to the primary position.

In fact, any mechanism that would serve to provide some resistance to the movement of the trailing end of the bone screw would ideally have to have several characteristics:

Firstly, it is ideal that whatever mechanism that is being implanted provides some resistance when the terminal portion of the bone screw is being compressed against the mechanism;

Secondly, whatever mechanism is utilized should be such that if the terminal portion of the bone screw moves in the opposite direction, the mechanism would force the wall of the chamber, or the plate (whichever embodiment is in place), back towards the head of the bone screw, i.e. back into it's primary position;

Thirdly, whatever mechanism is utilized must reproducibly provide the same amount of resistance to the motion segment;

Finally, in the most ideal embodiment, the mechanism can be converted to a fully stabilizing system with technical ease and facility.

Other embodiments of resistive mechanisms can be postulated by experts in the field. At this time, we remind all parties that such alternative mechanisms lie within the spirit and scope of the invention.

It is felt by the inventor that another important object of any such mechanism would be the ability of a surgeon to convert such a mechanism from a partially constrained stabilization system to a fully constrained stabilization/fusion system. As such, it would be important to be able to conveniently convert the system, after it has been implanted, from a partially constrained or dynamic stabilization system which allows for some, but not excessive, movement of a target motion segment to a system which does not permit any movement of the same target motion segment. Further clarifying, if the system is implanted in one of the preferred or alternative embodiments discussed herein, thus permitting for some movement of the target motion segment to a system that eliminates any movement of the target motions segment. In several of the embodiments above, this can be easily done (and in fact, certain instances percutaneously done) by removing whatever fluid medium is found in the chambers, and replacing that fluid medium with a biocement such as methylmethacrylate which once implanted will rapidly cure and prevent the movement of any parts within the chamber housing unit (and hence within the device itself). Upon curing of the methyl methacrylate, which occurs very rapidly, the resistive mechanism becomes an immobilizing mechanism and hence the entire system is converted from a system of dynamic stabilization or partially constrained movement to an immobile movement that would be best used for fusion. The inventor imagines that over time, there will be patients who may initially benefit from implantation of the dynamic stabilization system, but who would subsequently require a fusion.

It is clear when looking at some of the resistance mechanisms, that implantation of methylmethacrylate would be achieved with technical ease. This particularly applies to an embodiment in which the heads of the bone screws are incased within a single medium containing chamber. In such an embodiment, the medium is providing resistance to movement to the head of the screw, and thus resistance to the entire system. In this embodiment of the system, it can be imagined that the fluid medium could ostensibly be drained out, and replaced with methylmethacrylate within the chambers. Once the methylmethacrylate is completely cured, it essentially will preclude any movement of that motion segment. Obviously, this could also be done for embodiments in which there are multiple chambers, interfacing with the head of the screw.

Also, in some of the mechanical mechanisms such as the presence of a spring, again methylmethacrylate would serve to essentially immobilize such a mechanism and hence would again convert the system from the system of dynamic stabilization, or dynamic governors, to a system of utter immobility only useful in this setting of the fusion. While it might be speculated that in some of the mechanical mechanisms that were discussed above, infusing methylmethacrylate into the system may not be an optimal choice, and in fact may provide some harm, this is much more ostensibly theoretic than real.

There are primarily three different methods for implanting this invention into the spine of a patient suffering from spine disease. These methods vary in accordance with the embodiments of the device which are utilized in each of these methods. In each instance, the embodiment of the fully assembled invention is ostensibly the same, with the variation depending upon the fashion by which the device is implanted into the spine.

Hence, in the first method of implantation disclosed herein, the device is implanted by implanting various components and then assembling the device in situ. In such a proposed scheme, the screws or bone fasteners are first secured into the respective target pedicles. The chamber housing unit of the invention is then secured to the trailing ends of the two bone fasteners resulting in the completed construct. The method by which the chamber housing unit is secured to the trailing end of the bone fasteners is in part dependent upon the configuration of the trailing ends. In one embodiment that has been disclosed herein, the trailing most end of the bone fasteners is enlarged into a spherical, bulbous enlargement, which is past through an aperture on the chamber housing unit and into the chamber that shall house the trailing end. The aperture through which this bulbous enlargement shall pass is fitted with a gasket, and the inner diameter of the circle of the gasket is very slightly smaller than the greatest diameter of the bulbous enlargement of the trailing most end of the bone fastener. The gasket is made of a pliable or flexible material, such as polyethylene, latex, a flexible plastic, or any other such material, and hence, can transiently stretch and enhance the aperture and the gasket can be transiently stretched and enlarged as the bulbous end passes through. This will create a relatively irreversible coupling of the bulbous enlargement within its respective chamber. As the medium is then inserted into the walls of the chamber and expands the walls of the chamber, an even firmer coupling within the chamber occurs.

In one alternative embodiment, the gasket itself is part of the inflatable mechanism, and as the medium is passed into the chamber, the gasket, along with the walls of the chamber, are enlarged and hence, cradle the bulbous enlargement in a relatively irreversible coupling, merely allowing for the range of movement of the bulbous enlargement in a fashion corresponding to the range of movement of the bone fastener itself.

In yet another embodiment by which the device is assembled in situ is an embodiment in which the inflatable, ballotable chamber is not lining the walls of the chamber housing unit, but rather is found surrounding the bulbous enlargement of the trailingmost end of the bone fastener. In this embodiment, the bone fasteners are passed into place in the preferred position within the pedicles, following positioning of the bone fasteners within the pedicles, the chamber housing unit is then brought into place and secured over the bulbous enlargements found at the trailingmost end of the bone fasteners. The bulbous enlargements are now readily passed through the apertures in the chamber housing unit, and once secured into position within the chambers of this unit, the expandable membrane that surrounds the bulbous enlargement of the trailingmost end of the bone fasteners is filled essentially with the same types of media that were to be used for filling the walls of the chambers of the chamber housing unit.

The method by which the expandable membrane surrounding the trailingmost end is filled relates to an aperture that can be found anywhere along the shaft of the horizontal portion of the trailing end of the bone fastener. As stated, an aperture is found somewhat on the surface of the horizontal portion of the trailing end of the bone fastener. This aperture in turn, leads to an internal channel, which is fashioned through the center of the horizontal portion of the bone fastener, and is continuous with a central channel that is found in the terminal portion or bulbous enlargement. As stated, the external portion of the bulbous enlargement is surrounded with an inflatable balloon type expandable membrane. This is secured very adherently to the base of the bulbous enlargement; in this way, as the expandable membrane is enlarged using whatever medium is chosen, the seal at the base of the membrane will prevent the medium from leaking into the chamber or possibly out into the patient's body. It should be noted that all of the medium that have been proposed herein are quite safe and none of them are toxic such that should such a mishap occur and medium be exposed to the tissues, it is anticipated that this would cause no harm whatsoever.

Hence, the trailing end is inserted into the aperture in the chamber housing unit, and then the expandable membranes surrounding the trailing end is enlarged to the point that it fits very securely within the walls of the chamber. As the expandable membrane, which encases the bulbous enlargement, is filled with medium, this membrane expands against the walls of the chamber within the chamber housing unit. In this embodiment, the interior of the chamber can be contoured such that when the expandable membrane is fully enlarged, it fits snugly into the chamber, or there may be small spaces within the chamber after the expandable membrane is enlarged. Furthermore, the walls of the chamber can be padded, specifically with padding such as foam or microspheres, or for that matter, any other type sterile padding substance which is acceptable to the art. In such an embodiment, the constrained mobility of the system is provided by the relationship of the bulbous enlargement at the terminal portion of the screw to the medium environment surrounding it. In a fashion similar to the preferred embodiment previously described, the movement of the terminal portion of the screw is constrained by the medium through which it moves.

Such an embodiment could be seen in any of the three methods by which implantation of the device in its final form can occur. In addition, it is of course recognized that the walls of the chamber can also be expandable, ballotable walls as seen in other embodiments herein. Regardless, in this embodiment, it is anticipated that in the most ideal expression of this embodiment, the relationship of the expandable membrane when fully expanded to the interior of the chamber would be such that there would be permitted some movement of the bulbous enlargement, but that it would not be absolutely free to move in all planes. The restriction of movement is the ideal fashion by which the movement of the motion segment is constrained and brought back within physiologic range. Again, as has been proposed for other embodiments, it is expected that as further data and information is developed, it may be possible for a surgeon to identify a specific level of expansion of the dynamic mechanism which would be desirable and which would best serve the needs of the individual patient on a case-by-case basis. This again is in the spirit of the entire invention, which is to provide flexibility to the spine and multiple options to the surgeons.

Still further alternative embodiments can be contemplated. In yet another such embodiment, the bone fasteners are passed into the target pedicles. Prior to insertion of the trailingmost end of the bone fasteners into the chamber housing unit, a threaded nut or washer or combination thereof, is passed over the trailingmost end. In embodiments in which the trailingmost end is modestly enlarged or bulbous, it can be envisioned that the threaded nut, washer, or combination thereof, are already present on the horizontal portion or trailing vertical portion of the bone fastener. In any event, rather than relying on a pressure fit technology to secure the trailing end to the chamber housing unit, the chamber housing unit can be passed onto the trailing most ends and then these nuts and or nut/washer combination can then be secured in place around a threaded cuff, which is found at the side of the aperture to which the trailing end is passed. Such an embodiment would have to, in its final form, be carefully examined to be certain that it does not lead to a mechanical disruption in the desired movement of the trailing end of the bone screw. It must be recalled that because of the reciprocal action between the mechanism itself and the spine, limitation of range of movement by such a device could result in the limitation of the range of movement of the patient himself.

Yet even another embodiment for assembling in situ can be envisioned. In such an embodiment, the bulbous enlargement that is disclosed as being found on the trailingmost end of the bone fastener is, instead, an integrated component of the chamber housing unit. As such, in this embodiment, again a spherical component is illustrated. This spherical component is provided with an extension that is emitted from the chamber housing unit. This extension can then be coupled with the remaining trailing end of the bone fastener, that coupling being accomplished by a variety of techniques. It can be envisioned, for example, that the stem that arises from the rotatable sphere within the chamber housing unit may extend for a portion of the distance that would have been occupied by the full length of the horizontal portion of the trailing end of the bone fastener. Furthermore, the leading end of this stem, which is responsible for coupling with the trailing end of the remaining intact bone fastener, may be outfitted with a series of ratcheted like configurations, which in turn shall fit into a channel within the trailing end of the bone fastener. As the ratcheted embodiments are passed into the channel, it provides for an irreversible coupling of the two embodiments. Certainly any number of coupling mechanisms can be proposed for this component. It is recognized that this particular embodiment has several advantages—as do most embodiments. One advantage is that in this embodiment, with the sphere already in situ within the chamber housing unit, the chamber housing unit can be filled prior to implantation and the amount of "constrained motion" that is to be imparted upon the chamber housing unit can be determined by the surgeon prior to implantation. Again, it can be envisioned that this particular science may be advanced to the point that the fair accuracy, it can be predicted how much flexibility such a system should be given to an individual patient. In any event, yet another advantage of this particular embodiment is that it may reduce the length of the trailing end of the bone fastener, which would be exposed during insertion of the bone screw into the pedicles. It is understood that in an embodiment in which the horizontal portion of the trailing end is more than just 1.5-2 cm, then even under ideal circumstances, as the bone screw being passed into the pedicle, there is a very strong possibility that this horizontal extension will become entangled against or possibly engage the nearby facet joint. This would obviously be suboptimal.

Therefore, the smaller the horizontal portion (smaller because it is caused of two components that are reassembled after its insertion), then the less chance of entanglement engagement upon the facet joints. Certainly, one disadvantage that can be seen with a system such as this is that a coupling, no matter how strong, is weaker than an equal length of solid material, which is non-coupled. Obviously, therefore, this coupling could create a potential site of weakness, and potentially a point where the (combined) horizontal length of the trailing component of the bone fastener can become weakened, and ultimately fracture. This again would be considered suboptimal.

Hence, in this first method of implanting the invention into the spine of a surgical candidate, it can be appreciated that there are multiple ways by which this device can be inserted and then assembled.

The second method by which implantation of the device can ultimately result in reconstitution of the assembled device involves placement of the shafts of the screws in the respective pedicles, and then securing the chamber housing unit of the device, which is already containing the trailing ends of the bone fasteners, onto the trailing end of the screw shafts that have been implanted into the pedicles. In this embodiment, there is a junction of the pedicles and the chamber housing unit of the device, at some point along the reconstituted, reassembled, trailing end of the bone fastener. It can be imagined that this would most likely be comprised of a system by which the bone fastener is placed into the pedicle, with its trailing end exposed. The trailing end can be envisioned as having been provided with a sphere or any other geometric structure that can then be coupled. It is also envisioned that the dynamic mechanism, which is the same in all instances, which represents essentially the same types of embodiments in all instances, is then giving rise to what will ultimately be the trailingmost end of the bone fastener, when reconstituted. It is envisioned that in one embodiment, the screw is passed into the pedicle, with, as mentioned above, a trailing or terminal end that is spherical in shape. In this embodiment, the leading end of the shaft arising from the chamber housing unit is then provided with a cradle into which the sphere can relatively irreversibly "snap", resulting in reconstitution of the bone fastener and along with it, reconstitution of the entire construct. Other variations in which the junction can be envisioned in the horizontal portion or anywhere along the trailing end of the reconstituted bone fastener.

In the third fashion, by which the device can be implanted, the device is fully constituted, and is implanted as a single unit in which there is again a central portion of the bone fasteners coupled to the central portion. It is felt by the inventor that this is the preferred embodiment of the device.

In this, preferred embodiment, a mechanism must be provided for rotating the shafts of the bone fasteners and in that fashion, securing the device into its preferred position in the posterior aspect of the spinal column. Several preferred and alternative embodiments of a mechanism for rotating the screws will be provided. This embodiment may have several distinct advantages, primarily in eliminating the necessity to reassemble the device once the device has been at least partly implanted. Other clear advantages include the likelihood of a reduced operative time, which in turn reduces numerous complications such as those complications from anesthesia as well as infectious complications.

Therefore, in the preferred embodiment of the invention, the invention is represented by two bone fasteners, or bone screws, which can be inserted into the pedicles and thus, secure the device to the spine itself. In this embodiment, the device largely resembles a device that has been described throughout this application. In furtherance of that concept, we note that this embodiment has two bone fasteners that pass into the pedicles on their long axis. In this embodiment, the bone fasteners are comprised of multiple components. These bone fasteners are designed such that when they have been passed into the pedicles of the maximum allowable depth, there is a portion of the bone fastener above the entry point into the bone. That portion of the bone fastener can arise and proceed along the same axis as the long axis of the screw for a small period of time, at which point it assumes a curve and into a horizontal line, and then at variable degrees and angles, is directed posteriorly. In such an embodiment, the trailingmost end of the bone fastener is encased within a chamber which is within the cylindrically shaped central portion of the invention. The interface between the trailingmost end, the bone fasteners, and the interior of this chamber has already been utterly discussed, and in this embodiment, all measures are taken to maintain the interface between the trailing most end of the bone screw and the chamber that has been previously described.

The critical aspect of this particular embodiment involves the mechanism by which involves the mechanism by which the shafts are the screws can be rotated while maintaining the stability of the ridging component of the invention, which is the central chamber. It is envisioned that in the most preferred embodiment of this invention, the long shaft of the screws terminates in a spherical shaped structure. This spherical structure is, in reality, encased within a cradle which is found on the leading end of the next portion of the bone fastener. In this multi-component embodiment, there is a junction between the bone screw and the intermediate portion, which ultimately results in permitting the shaft of the bone screw to be rotated without rotating the intermediate portion that interfaces with the shaft. It is envisioned that the junction between the intermediate portion and the shaft occurs just above the entry point of the shaft into the bone pedicle.

As mentioned, there is an intermediate component, which lies between and couples to both the bone screw and the chamber housing unit of the invention. This central portion is composed of the trailingmost end of the reconstituted bone screw, or the trailing end of the intermediate, which is a spherical structure and lies within the chamber of the chamber housing unit of the device. This monolithic structure emerges from the chamber housing unit of the invention, and a small length of the intermediate component extends from the trailingmost portion, which is within the chamber of the central component, and extends to the junction of the intermediate component with the trailing end of the shaft of the bone fastener. it is anticipated that in the ideal embodiment, from the spherical portion that is within the chamber of the chamber housing unit of the device, the intermediate portion exists in a somewhat eccentric fashion and is then continuous with a horizontal portion, which then leads into the leading portion of this component, that portion then defined by a curvature into the proximal portion that is approximately orthogonal to the horizontal portion of this component, and continuous with the long axis of the bone fastener.

Pedicle Trocar

The pedicle trocars have already been disclosed but are again reviewed in this section for completion purposes. There are two principle components of the pedicle trocars, an inner shaft, and an outer sheath. The inner shaft has at its trailing end a rotatable handle which is then coupled to a drive shaft that passes through a channel located within the center portion of the outer sheath. At the leading most end of the inner shaft is a pointed trocar, which may be monolithic with a short threaded cylinder. These areas are the only areas which are radiopaque. At the trailing end of the assembled device is found a bracket which can be reversibly coupled to the trailing end to adjust the amount of the inner shaft that is protruding from the leading end. This is specifically so that the device can be initially passed through the muscles and soft tissue of the back with the leading end retained within the cone-shaped leading end of the outer sheath. Once the device is in position, the bracket can be removed and the inner shaft can be deployed by the surgeon penetrating the base or entry point of the pedicle. When this has been sufficiently accomplished, the inner shaft can be removed.

In one embodiment, the outer sheath has a removable panel along the side which faces the other pedicle trocar. This removable panel can be removed to facilitate passage of the unitized assembled invention. The screws would be passed down through the central channels of the outer sheaths and the defect created by removal of the removable panels accommodates the diagonal connectors.

The critical aspect of the leading end being the only portion that is radiopaque is that this will allow intra-operative identification much more easily.

Alternatively, the leading end of the inner shaft is again a trocar is continuous and monolithic with a central shaft which is then continuous with the trailing end which is the rotatable handle found at the trailing end of the assembled device. The outer sheath is then passed over the central shaft and in this way forms the outer aspect of the assembled device. The leading end of the outer sheath is tapered such that this leading end, in combination with the leading end of the trocar, assumes a substantially tapered configuration that is easily insinuated through the soft tissues along the tract from the skin to the entry point in the bone at the base of the pedicle.

In this embodiment, the assembled device is configured such that the taper of the inner shaft and the outer sheath are continuous and confluent. The trailing end of the inner shaft is expanded at the exact point where the outer sheath ends, thereby allowing the assembled device to be advanced as a unit. In this fashion, the assembled device is advanced until leading end of the inner shaft is advanced into the pedicle. The assembled device is further passed until the leading end of the outer sheath is brought against the bone. At that point, the inner shaft is removed.

Retractor

A unique, purpose-specific retractor is provided with this disclosure. This will actually be more fully described in a separate application, but briefly this device is a substantially-triangular shaped device (as viewed from the top plane) which is provided with a unique hydraulic or pneumatic expansion mechanism which permits expansion of the retractor both in the craniocaudal direction, as well as in terms of depth of the incision. Additionally, the superior and inferior aspects are configured to recapitulate the shape of the outer sheaths of the pedicle trocars. It can be recalled from the "surgical technique" section that the superior and inferior aspects of the refractor stabilize the pedicle trocars during insertion. The triangular shape accommodates the insertion handle.

Insertion Apparatus

This is another uniquely-designed, purpose specific apparatus utilized in the implantation of the invention. It will be disclosed completely in a separate application, but it is necessary to disclose it in some succinct fashion here, so that at least its role in the implantation of the invention may be understood.

This handle is designed to insert the unitized invention through the purpose-specific retractor and stabilize the chamber housing unit while inserting the bone fasteners into the pedicles. The device is provided with a unique, twin-screwdriver embodiment that has been previously disclosed by the inventor in a US Provisional Application filed with the United States Patent and Trademark Office on Feb. 1, 2006 entitled "Unitized System for Reconstruction of Osseous Fracture Fragments," which has been assigned provisional No. 60/764, 758.

In order to accomplish these and other objects of the invention, this handle has been provided with a leading end, a shaft, and a trailing end. The leading end is further provided with a stabilizing clamp which can be reversibly coupled with the body of the chamber housing unit. In its preferred embodiment, this clamp is provided with a superior stabilizing jaw that is placed on the upper, flattened aspect of the chamber housing unit, with a second jaw, an inferior stabilizing jaw, placed on the inferior surface of the unit. By a spring-loaded mechanism, a ratcheting mechanism, or any other such mechanism acceptable to the art, the two jaws are compelled towards each other. In this fashion, the jaws are able to maintain the chamber housing unit between them in a stable, secure fashion. A shaft is then provided which extends from the securing mechanism to the trailing end of the insertion handle, where this shaft couples with a handle designed to release the jaws once the invention has been implanted and secured into the bone.

The device is secured into the bone with the use of twin screwdrivers that have also been provided and are incorporated into the insertion handle. This aspect of the invention is best described by recognizing that there is a trailing end which has been provided with a rotatable handle. This is then coupled with a shaft which is fashioned to translate the rotations of the handle from the trailing end of the shaft to the leading end.

At the leading end of the shaft is found a beveled gear, which rotates in an equivalent rotation with the rotatable handle. The bevel of this gear is generally oriented downward towards the leading end of the insertion handle. This beveled gear will, in turn, interface with two upward-oriented beveled gears that are located at the lateral edges of the insertion handle bilaterally. These are then continuous with and translate the rotation to rotatable shafts, which are consequently rotated by the rotation of the gears. Screwdriver/Philips head configurations/hex screw configurations are located at the leading ends of these two shafts. Therefore, this configuration allows rotation (by the operator) of the handle at the trailing end of the insertion handle to result in rotation of the screwdriver insertion devices, thus resulting in passing the screws into the target pedicles.

The entire device is provided with a frame which serves to stabilize the invention while the screws are being inserted. Included in this frame is an outer sheath which covers the shaft leading from the rotatable handle to the beveled gear. This outer sheath is so fashioned such that it can be used as a handle by the surgeon, and is provided with a central channel which has a sufficient diameter so that the shaft extending from the rotatable handle to the beveled gear may rotate unimpeded. The insertion handle is also configured such that the jaws mechanism which stabilizes the chamber housing unit is part of the outer frame, and holds the chamber housing unit at an optimal level such that the leading ends of the twin screws readily pass through the insertion apertures of the diagonal connectors and interface with the insertion surface of the pedicle screw. The invention is maintained in position by the stabilizing jaws during insertion.

In an alternative embodiment, the pedicle trocar is comprised of two elements, an inner element which is a central trocar and an outer sheath. The central trocar is provided with a leading end, a shaft, and a trailing end. The leading end is comprised of a metal component of sufficient strength to penetrate the entry point to the pedicle. The outer sheath is itself modular, and once the inner sheath is in good position, the outer sheath can be disarticulated and forms part of the retractor. Two additional components of the retractor are then added, the retractor is stabilized, and the procedure is completed.

What is claimed is:

1. A spinal implant device for the creation or restoration of the natural motion of a target motion segment, the spinal implant device comprising:
   a first diagonal connector with a first leading end, a first spherical enlargement, and a first pedical screw extending from the first diagonal connector
   a second diagonal connector with a second leading end, a second spherical enlargement, and a second pedical screw extending from the second diagonal connector; and
   a fluid chamber housing unit comprising
      a first fluid chamber with a first access port, wherein a first lining is disposed within the first fluid chamber and comprises a first diaphragm aligned with the first access port to permit introduction of fluids to the first fluid chamber, the first fluid chamber having a first receptacle housing the first spherical enlargement of the first diagonal connector such that the first leading end contacts the first lining;

a second fluid chamber with a second access port, wherein a second lining is disposed within the second fluid chamber and comprises a second diaphragm aligned with the second access port to permit introduction of fluids to the second fluid chamber, the second fluid chamber having a second receptacle housing the second spherical enlargement of the second diagonal connector such that the second leading end contacts the second lining;

an immobile wall separating the first fluid chamber from the second fluid chamber such that fluids disposed therein are fluidically isolated.

* * * * *